United States Patent
Tesar

(10) Patent No.: US 11,396,928 B2
(45) Date of Patent: Jul. 26, 2022

(54) ACTUATOR WITH A PARALLEL ECCENTRIC GEAR TRAIN DRIVEN BY A MECHANICALLY AMPLIFIED PIEZOELECTRIC ASSEMBLY

(71) Applicant: Delbert Tesar, Austin, TX (US)

(72) Inventor: Delbert Tesar, Austin, TX (US)

( * ) Notice: Subject to any disclaimer, the term of this patent is extended or adjusted under 35 U.S.C. 154(b) by 159 days.

(21) Appl. No.: 16/512,345

(22) Filed: Jul. 15, 2019

(65) Prior Publication Data
US 2020/0080621 A1    Mar. 12, 2020

Related U.S. Application Data

(60) Provisional application No. 62/698,192, filed on Jul. 15, 2018.

(51) Int. Cl.
| | | |
|---|---|---|
| *F16H 1/46* | (2006.01) | |
| *A61B 17/29* | (2006.01) | |
| *H02N 2/04* | (2006.01) | |
| *A61B 17/00* | (2006.01) | |
| *F16H 57/10* | (2006.01) | |
| *A61B 34/30* | (2016.01) | |

(52) U.S. Cl.
CPC .............. *F16H 1/46* (2013.01); *A61B 17/29* (2013.01); *F16H 57/10* (2013.01); *H02N 2/046* (2013.01); *A61B 2017/00398* (2013.01); *A61B 2017/2943* (2013.01); *A61B 2017/2947* (2013.01); *A61B 2034/302* (2016.02)

(58) Field of Classification Search
CPC . F16H 1/46; A61B 17/29; A61B 2017/00398; A61B 2017/2943; A61B 2017/2947; H02N 2/046

USPC .......................................................... 74/640
See application file for complete search history.

(56) References Cited

U.S. PATENT DOCUMENTS

| | | | | |
|---|---|---|---|---|
| 6,075,759 | A | 6/2000 | Yanagawa et al. | |
| 6,424,886 | B1* | 7/2002 | Iversen | A61F 2/585 |
| | | | | 700/254 |
| 6,491,601 | B1* | 12/2002 | Moskob | F16H 1/32 |
| | | | | 475/162 |
| 6,664,710 | B1* | 12/2003 | Gottlieb | H02N 2/105 |
| | | | | 310/323.02 |
| 7,326,143 | B2* | 2/2008 | Kimura | F16H 1/32 |
| | | | | 475/149 |

(Continued)

FOREIGN PATENT DOCUMENTS

| | | |
|---|---|---|
| DE | 1387204 | 3/1975 |
| DE | 102010003720 A1 | 6/2011 |

OTHER PUBLICATIONS

Lande, P. R., K. P. Toradmal, and F. A. Pathan. "Study of Compliant Mechanisam." International Journal of Innovative Research in Science, Engineering and Technology 3, No. 4 (Apr. 2014): 53-60.

(Continued)

*Primary Examiner* — Ha Dinh Ho
(74) *Attorney, Agent, or Firm* — John A. Fortkort; Fortkort & Houston PC

(57) ABSTRACT

An actuator is provided which includes a parallel eccentric gear train, a prime mover having an assembly of piezoelectric elements which drives the gear train and which forms a mechanical amplifier, and a crankshaft which is driven by the parallel eccentric gear train.

20 Claims, 21 Drawing Sheets

(56) References Cited

U.S. PATENT DOCUMENTS

| | | | |
|---|---|---|---|
| 7,456,549 B2 * | 11/2008 | Heim | H02N 2/101 |
| | | | 310/328 |
| 7,695,389 B2 * | 4/2010 | Fleytman | H02N 2/105 |
| | | | 475/178 |
| 8,664,831 B2 | 3/2014 | Blume et al. | |
| 8,764,680 B2 | 7/2014 | Rhad et al. | |
| 8,998,682 B2 | 4/2015 | Christopher et al. | |
| 2002/0029060 A1 | 3/2002 | Hogendijk | |
| 2002/0166542 A1 | 11/2002 | Kirzhner et al. | |
| 2002/0196569 A1 | 12/2002 | Eliahu-Niv et al. | |
| 2003/0048037 A1 | 3/2003 | Boyd | |
| 2004/0045148 A1 | 3/2004 | Moler | |
| 2004/0140737 A1 | 7/2004 | Barillot et al. | |
| 2006/0175934 A1 | 8/2006 | Or et al. | |
| 2007/0033682 A1 | 2/2007 | Sretavan et al. | |
| 2007/0149881 A1 | 6/2007 | Rabin | |
| 2010/0038995 A1 | 2/2010 | Claeyssen et al. | |
| 2010/0133957 A1 | 6/2010 | Schuh et al. | |
| 2010/0148630 A1 | 6/2010 | Petrenko et al. | |
| 2011/0204120 A1 | 8/2011 | Crainich | |
| 2011/0285248 A1 | 11/2011 | Cewers | |
| 2012/0017688 A1 | 1/2012 | Shekalim | |
| 2012/0187802 A1 | 7/2012 | Moler et al. | |
| 2013/0095732 A1 | 4/2013 | Christopher et al. | |
| 2013/0186932 A1 | 7/2013 | Shelton, IV et al. | |
| 2013/0336820 A1 | 12/2013 | Griffin et al. | |
| 2014/0025089 A1 | 1/2014 | Sholev | |
| 2014/0130773 A1 | 5/2014 | McAlister | |
| 2014/0255985 A1 | 9/2014 | Oldham et al. | |
| 2014/0306576 A1 | 10/2014 | Ervin et al. | |
| 2015/0069144 A1 | 3/2015 | McAlister | |
| 2015/0076965 A1 | 3/2015 | Culpi | |
| 2015/0097467 A1 | 4/2015 | Griffin et al. | |
| 2015/0133739 A1 | 5/2015 | Piskun et al. | |
| 2015/0187349 A1 | 7/2015 | Schafer | |

OTHER PUBLICATIONS

Mali, Girish Suresh. "Novel Escapement Mechanism using a Compliant Mechanism and a Piezoelectric Actuator." (2007).

Ouyang, Puren & Zhang, W. & Gupta, Madan. (2005). Design of a New Compliant Mechanical Amplifier. Proceedings of IDETC/CIE, DETC2005-84371. 10.115/DETC2005-84371.

Ouyang, Puren & Zhang, W. & Gupta, Madan. (2008). A New Compliant Mechanical Amplifier Based on a Symmetric Five-Bar Topology. Journal of Mechanical Design—J Mech Design. 130.10. 1115/1.2965600.

Eskandari, Amiraslan (2013): Design and optimization of compliant mechanical amplifiers. Ryerson University. Thesis. https://doi.org/10.32920/ryerson.14646435.v1.

* cited by examiner

ACTUATOR WITH A PARALLEL ECCENTRIC GEAR TRAIN DRIVEN BY A MECHANICALLY AMPLIFIED PIEZOELECTRIC ASSEMBLY

CROSS-REFERENCE TO RELATED APPLICATION

This application claims the benefit of priority of U.S. provisional application No. 62/698,192, filed Jul. 15, 2018, having the same inventor and the same title, and which is incorporated herein by reference in its entirety.

FIELD OF THE DISCLOSURE

The present disclosure relates generally to electromechanical actuators, and more particularly to actuators equipped with a parallel eccentric gear train that is driven by a piezoelectric assembly through mechanical amplification.

BACKGROUND OF THE DISCLOSURE

Surgery clearly demands the highest form of physical task performance. This requires exceptional actuators with intelligence to respond rapidly/accurately to the surgeon's commands. Virtually all present laparoscopic systems are cable driven with performance deficits due to numerous pulleys (high friction), difficult sterilization, insufficient stiffness, and are not MRI compatible, etc.

Several attempts have been made to miniaturize actuators. Two German/Swiss companies (Faulhaber, Maxon) have a strong market penetration for small actuators leveraging the feinwerk tecknik of the watch industry. Unfortunately, that technology is a refinement of an old tech base with many weaknesses that prevent it from being able to adequately meet the needs of laparoscopic surgery.

Other attempts have also been made to produce miniaturized actuators. However, these attempts have failed to yield actuators with sufficiently high dexterity, precision, force levels and smoothness, and sufficiently low weight, to make them suitable for surgical applications.

SUMMARY OF THE DISCLOSURE

Figure 1:
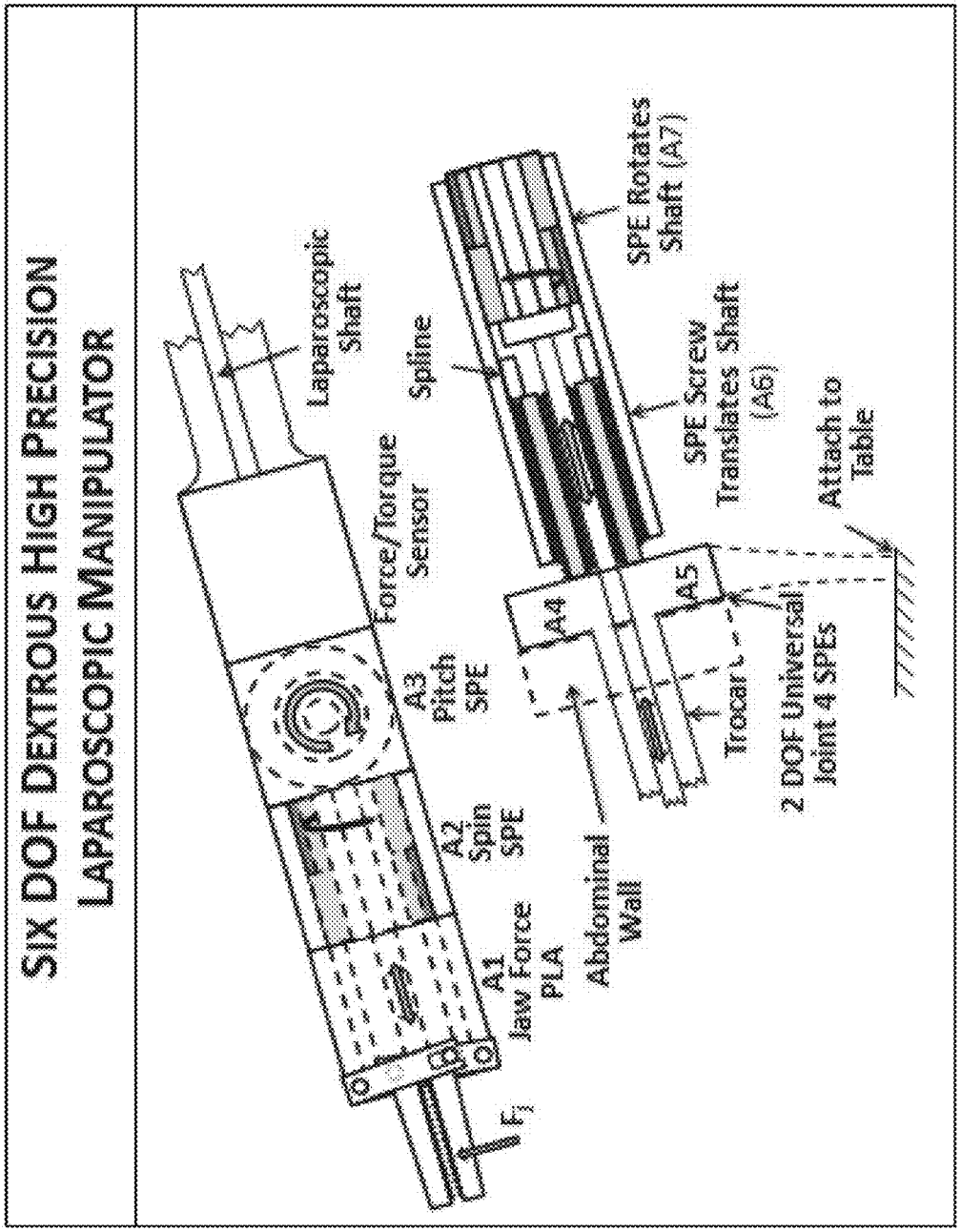
FIG. 1 is an illustration of an embodiment of a six degrees of freedom high precision laparoscopic manipulator.

In one aspect, an actuator is provided which comprises (a) a parallel eccentric gear train; (b) a prime mover having an assembly of piezoelectric elements which drives said gear train and which forms a mechanical amplifier; and (c) a crankshaft which is driven by said parallel eccentric gear train.

In another aspect, an actuator is provided which comprises (a) a parallel eccentric gear train; and (b) a piezoelectric structure that drives said gear train, said piezoelectric structure including a mechanical amplifier.

In a further aspect, an actuator is provided which comprises (a) first and second parallel eccentric gears; and (b) a plurality of compliant linkage amplifiers which drive said first and second parallel eccentric gears; wherein said first and second parallel eccentric gears oscillate 180° out-of-phase and without rotation to generate eccentric motions.

In still another aspect, an actuator is provided which comprises (a) first and second opposing endplates; (b) a rotor having first and second eccentrics on a surface thereof; (c) an output gear disposed about the periphery of said first and second opposing endplates; (d) a first parallel eccentric gear which is disposed between said first eccentric and said output gear and which meshes with said output gear; (e) a second parallel eccentric gear which is disposed between said second eccentric and said output gear and which meshes with said output gear; (f) a first crosslink which engages said first endplate and said first eccentric gear by way of a first set of surface features; (g) a second crosslink which meshes with said second endplate and said second eccentric gear by way of a second set of surface features; and (h) at least one piezoelectric structure having a first set of piezoelectric elements which drives at least one of said first and second parallel eccentric gears, and a second set of piezoelectric elements which form a mechanical amplifier that drives the first set of piezoelectric elements.

DETAILED DESCRIPTION

It has now been found that the foregoing needs may be addressed with the actuators disclosed herein. In a preferred embodiment, these actuators provide a laparoscopic manipulator which may be placed under direct control of the surgeon, and which has high dexterity, precision, force levels, and smoothness, and weighs no more than 5 pounds. A preferred embodiment of this manipulator uses seven similar piezoelectric prime movers, combined with exceptional gear trains (all MRI-compatible), to make standardized actuators of ever-increasing performance in minimum sets to reduce cost, provide for rapid repair, and allow for simple sterilization.

A mechanical displacement amplifier integrated with a piezoelectric (PZT) actuator is very compact in size, and is typically capable of producing high displacement resolutions and low-strain and high-force outputs. A disadvantage of PZT actuators is their relatively short motion ranges (typically about 15-20 μm), which is insufficient for many engineering applications. It has been found that this disadvantage may be overcome by the use of a displacement amplification mechanism.

A promising building block of such an amplification mechanism is the compliant mechanism. A primary design goal of the amplification mechanism is to achieve a large amplification ratio. This goal may, however, compromise the generated force and natural frequency of the system. Reduction in the generated force may be tolerated, as a PZT actuator can provide a large force. Therefore, the more practical design goal of an amplification mechanism is a twofold goal of providing a large amplification ratio and a high natural frequency.

A stepping motion amplifier mechanism, coupled with an integrated ratchet-type transmission linkage, transforms the step motion into a rotational displacement with high torque properties. A mechanical amplifier is an important device which, in conjunction with a piezoelectric actuator, may achieve motion with high resolution and long range. A new topology is proposed herein which is based on a symmetric five-bar structure for displacement amplification, and a compliant mechanism is utilized for the amplifier. In short, the new mechanical amplifier is called a compliant mechanical amplifier (CMA). Compared to existing CMAs, preferred embodiments of the CMAs disclosed herein may achieve large amplification ratios and high natural frequencies in terms of topology.

In order to meet the performance goals of laparoscopic surgery, a significant improvement has been needed in piezoelectric-driven actuators. This is achieved by preferred embodiments of the systems and methodologies disclosed herein through the provision of exceptional gear reducers. These gear reducers are equipped with only one pair of rolling element bearings that are 15× more load capable in all six directions than tapered roller bearings. The reducer is a simplified parallel eccentric with only 5 basic parts (two oscillating eccentric gears, a rotating output gear and two constraining cross links), all of which, in one particular, nonlimiting embodiment, are assembled into a 0.4" diameter and 0.4" long module. This module may either be used for a rotary or a linear output to generate very high design forces (for example, 40 (+) oz-in. torque or 40 lb. linear force). All of this may be achieved with high accuracy, exceptional responsiveness, high stiffness, and no backlash. These actuators may be made with MRI-compatible materials in minimum sets to reduce cost in quantity production. These actuators may be highly certified to meet application specifications, and may provide real-time data feedback in millisec. to the surgeon. The overall weight of the 7 DOF system (which, in a preferred embodiment, includes a gripper, a 2 DOF wrist, force/torque sensors, a 2 DOF universal joint at the trocar, and 2 external DOF for translation/rotation of the laparoscopic shaft) is approximately 5 lb in one embodiment.

Beyond this 7 DOF surgical laparoscope, another key subsystem is the manual controller. This controller preferably provides two-way information transfer from the surgeon to/from the system. The missing technology in such controllers has been force feedback, which is 50% of what the surgeon requires to be fully capable of complex surgery.

A recent survey of 75 papers in the literature on robotic surgery listed a number of significant limitations in the current technology. These limitations include the cost of such systems, the excess staff requirements for their use, their size, the lack of force feedback they provide to the surgeon, their lack of dexterity and MRI compatibility, their low stiffness, and the extensive training required for their use.

Out of this study, some key recommendations were made. It was noted that robotic surgery requires high accuracy, visual feedback, force feedback, lightweight/smaller devices, lower cost (⅔ less), high tool force levels, high stiffness, plug-and-play repair, the ability to archive all operations and obtain lessons learned, minimum component sets, distributed low-cost sensors, an improved master controller, and MRI Compatibility.

It is clear from the foregoing literature survey that a new technology is now required to provide major performance improvements for robotic surgery. All of the limitations and recommendations listed above have been taken into account in preferred embodiments of the robot laparoscopic system described here. A key component of these systems is intelligent actuators, which is part of the basis for the "modular" robot represented as a laparoscopic system in FIG. 1.

While some existing actuators may be considered miniaturized, it has been found that a preferred embodiment of the piezoelectric SPE disclosed herein beats its best competitor by 600×, and its weakest competitor by 130,000×. This is the basis for the claim that real progress can now be made in robotic surgery. The provision of exceptional actuators of this type mean that all cable drives may be superseded where direct joint control confirms that high positional accuracy and quick responsiveness to command may now be possible. Friction issues disappear or become negligible. Information flow may now occur in 10 msec. Moreover, as these actuators improve, they may be rapidly inserted into existing systems at relatively low cost to envision a continuous pathway for technical performance growth.

Fundamentally, the miniature actuator tech base disclosed herein includes a set of piezoelectric amplifier linkages as the prime mover to oscillate a pair of parallel eccentric gears. These PE gears then drive an internal output gear. At this small scale, the shape of the meshing teeth is typically not critical. Since the eccentric gears only oscillate at a small amplitude (with no rotation), their effective inertia is small, making them very responsive to command. The rotation constraint is preferably provided by a cross link which has tongue and groove splines therein to mesh with the gears and the stationary end plates. These splines may be preloaded in a simple manner with a wave spring disposed between the two eccentric gears to eliminate any backlash. The piezoelectric amplifiers may create large forces to generate sufficient input energy to the eccentric gears. Generally, with a reduction of 100-to-1, the output torque in these systems is found to be quite high, and its magnitude is constrained primarily by the shearing strength of the short teeth.

For the envisioned basic actuator size (an actuator 0.4" in diameter and 0.4" long would typically be suitable for this application), the design torque for a preferred embodiment would be 40 oz-in. with a peak of about 100 oz-in. Given an output range of motion of 90° per second, this requires a piezoelectric driving frequency of 25 hz or 1500 cycles per minute, which is quite modest. Fortunately, the duty cycle for these actuators under human control is typically not very demanding, so that endurance and temperature control should typically not be issues. For example, to hold a force with a 100-to-1 reduction puts no energy demand on the piezoelectric drivers. Further, the Simplified Parallel Eccentric (SPE) (described in US2017/0271948 (Tesar), which is incorporated herein by reference in its entirety) requires only two miniature rolling element bearings (to support the rotating output shaft) outside the load path to make this miniature actuator simple and very rugged.

A useful version of a miniaturized linear actuator with high ruggedness, efficiency, and force density is described herein. Its transmission is a very small planetary screw now produced in the U.S. by Creative Motion Control. The inner screw becomes the translating output shaft (without rotation). The nut (or outer shell) of the transmission is also the rotor of the BLDC motor to drive the actuator. The rotor does not translate due to sophisticated grooved roller bearings at each end (also made by Creative Motion Control) A reasonable diameter for this existing technology would be 0.8", which is quite useful for an external linear drive outside the human body for laparoscopes.

Handheld tools used by surgeons and endodontists are usually specialized passive tools. Hence, the manual dexterity of the trained surgeon is typically critical. Unfortunately, these physical commands contain tremors and errors. This error content increases with the difficulty and length of the operation. Development of intelligent handheld tools has been ongoing for two decades. Two advanced solutions for handheld tools and described herein which utilize the tech base for miniaturized actuators noted above.

The 2 DOF endodontic tools and the surgical tools described herein preferably utilize a Linear Planetary Screw (LPS) for tool translation, and the SPE for tool rotation of the end instrument. In both cases, complex motion features in motion range (such as, for example, forward/reverse, speed, and force/torque levels) may be set by voice commands of the operator. Each tool will preferably be equipped with quick-change instrument connections to a force/torque sensor. For the surgical tool, LED optics and inertial sensors may be utilized to provide real-time data to compensate for tremors and errors. Given this capability, training may be accelerated, because the operator would have immediate feedback on correct operational commands. These handheld tools are a great testing opportunity to evaluate needed sensors and actuators (and associated software) that would then become useful in laparoscopic surgical systems.

FIG. 1 depicts a first particular, nonlimiting embodiment of a 6 degree of freedom (DOF) dexterous high precision laparoscopic manipulator in accordance with the teachings herein. While dimensions and physical characteristics are provided for this particular embodiment and its components for illustration purposes, one skilled in the art will appreciate that these dimensions and characteristics are not limiting, and may be adjusted as necessary to accommodate the application in which the laparoscopic manipulator will be utilized.

The laparoscopic manipulator depicted in FIG. 1 is an intelligent system designed for small incisions (typically about 0.5") during internal abdominal surgery. Other uses of this device are also contemplated, using the basic components (actuators, sensors, grippers, etc.) and system technology (force feedback, haptic interface, operational software, surgeon task visualization, lessons learned from archived data, etc.). This 6 DOF laparoscopic manipulator (with one additional DOF for the gripper) is equipped with a straight shank to pass through the trocar. No cables are required, leaving the shank open for electrical power and communication lines. All joints are directly driven by self-contained actuators, thus enabling future plug-and-play modularity for an upgradable, easily repaired and sterilized architecture.

The laparoscopic manipulator of FIG. 1 is designed to be rapidly replaced using an alternate emergency power supply and control to back drive the failed actuators. The layout uses seven actuators. Thus, actuator A1 is a piezo drive SPE with screw output shaft to create a large linear force to drive the gripper (0.4" d×0.4" l, design force 40(+) lbs). Actuator A2 is a piezo drive SPE which creates a roll DOF for spin of the gripper to enhance suturing type functions (0.4"d× 0.4"l, generates 40 oz.-in torque and 100 oz-in peak). Actuator A3 is a piezo drive SPE which acts as a pitch actuator with a range of ±90° (or greater) to enable large volume working space at the end of the system's shank (the same as actuator A2). Actuators A4 and A5 are piezo driven actuators which drive a universal joint cross link holding the trocar to enable 3 to 5 lb. lateral forces at the gripper (0.75"d×1.0" l, each generates 400 oz-in. torque, 1000 oz-in. peak). Actuator A6 uses a piezoelectric ring prime mover with amplifier linkages to form a SPE with an output screw shaft to translate the system shank through the trocar (0.75" d×1.0" l, generates 40(+) lb. force). Actuator A7 uses a piezoelectric SPE to rotate the system shank. It slides on an external spline on the outside of A6 to prevent relative rotation (0.75" d×1.0" l, generates 400 oz-in. torque and 1000 oz-in. peak).

One other notable component is the F/T sensor attached between actuator A3 and the system shank. A special 10 mm (0.4") F/T sensor may be utilized here. It is to be noted that all these actuators are piezoelectric driven SPEs (Simplified Parallel Eccentrics). They may be fabricated from suitable materials such as, for example, ceramics, plastics, and stainless steel. Ceramic rolling element bearings are available. Plastics may be utilized for the actuator shells for low weight, and stainless steel may be utilized for bearing races gears, and sliding splines. All of this suggests that these SPEs will be MRI compatible.

Figure 2:
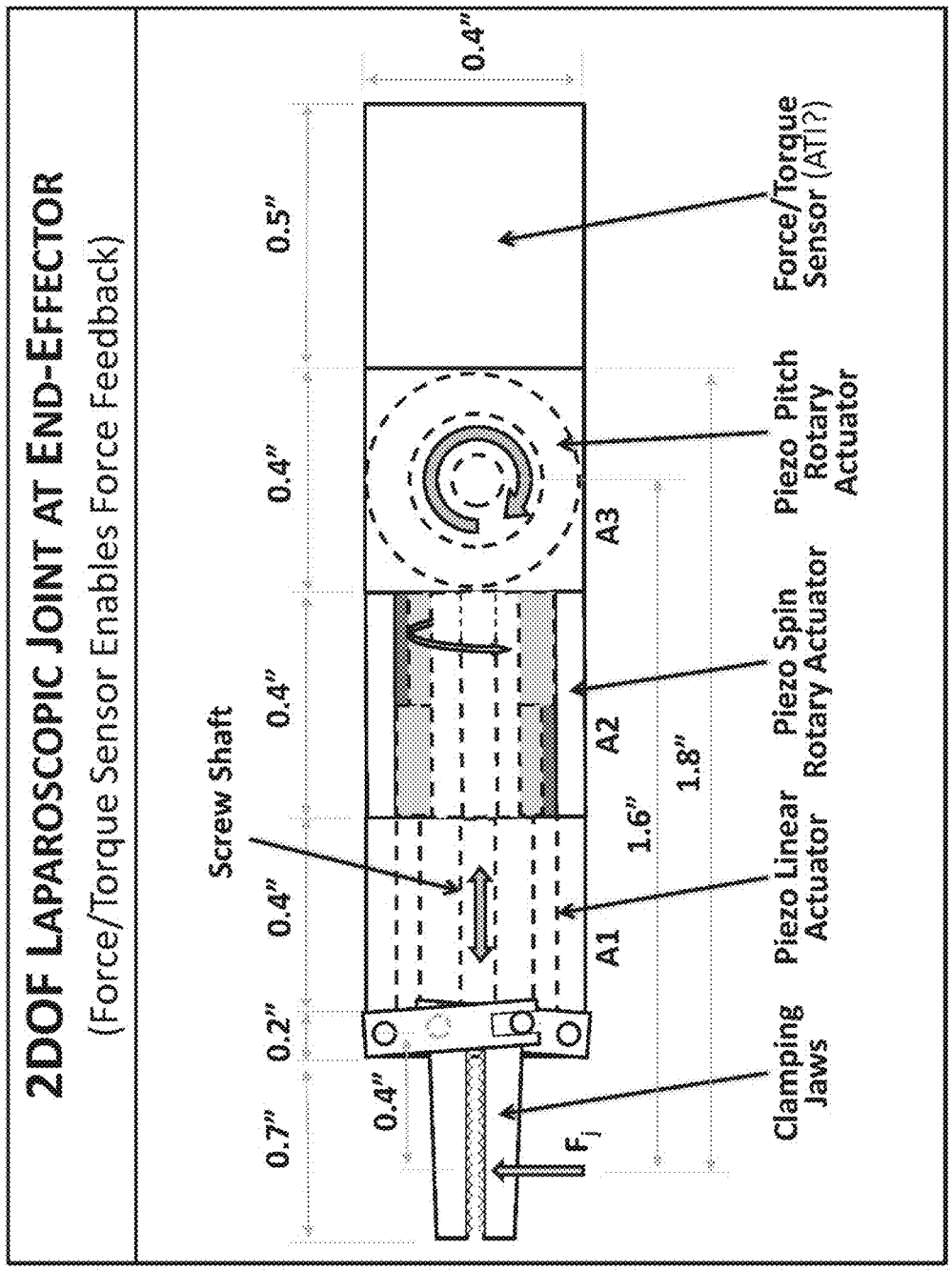
FIG. 2 is an illustration of an embodiment of a two degrees of freedom laparoscopic joint at an end effector equipped with a force/torque sensor that enables force feedback.
Figure 3:
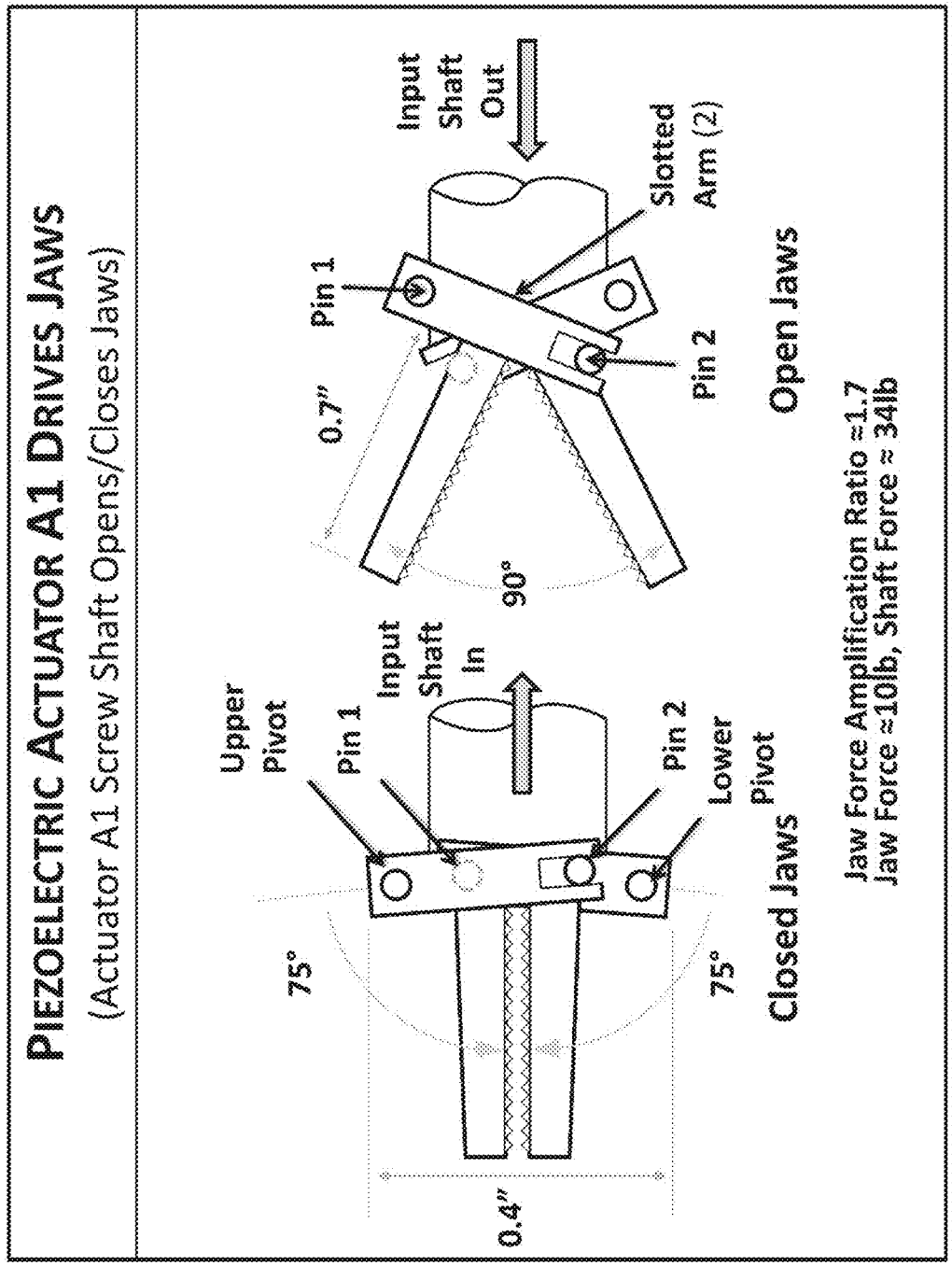
FIG. 3 is an illustration of an embodiment of piezoelectric actuator drive jaws; an actuator screw shaft opens and closes the jaws.

FIG. 2 provides a more detailed layout of the 3 DOF end-effector with the F/T sensor. The gripper design is notable, since it is required to create a large 10 lb. jaw force $F_j$ at a distance of 0.4" from its anchor pins. FIG. 3 shows the gripper in its closed position (the drive screw shaft is now moved into A1), and its 90° open position (the drive screw shaft, is now moved out of A1). The drive screw shaft holds two pins which are in arm slots in the jaw clamps which, when translated, open and close the jaws. Each jaw clamp is pivoted about a pin in a special housing attached to actuator A1 with a quick release mechanism which enables the whole gripper assembly to be unscrewed from the A1 drive mechanism for simple sterilization. Each jaw clamp is oriented by a 75° angle from the slotted arm to allow a 15° swing to the right and 30° swing to the left to maximize the gripper's mechanical advantage (i.e., the moment arm from the screw shaft pin and the jaw pivot). This force amplification ratio is approximately 1.7. The total length of the jaw is preferably 0.7".

Figure 4:
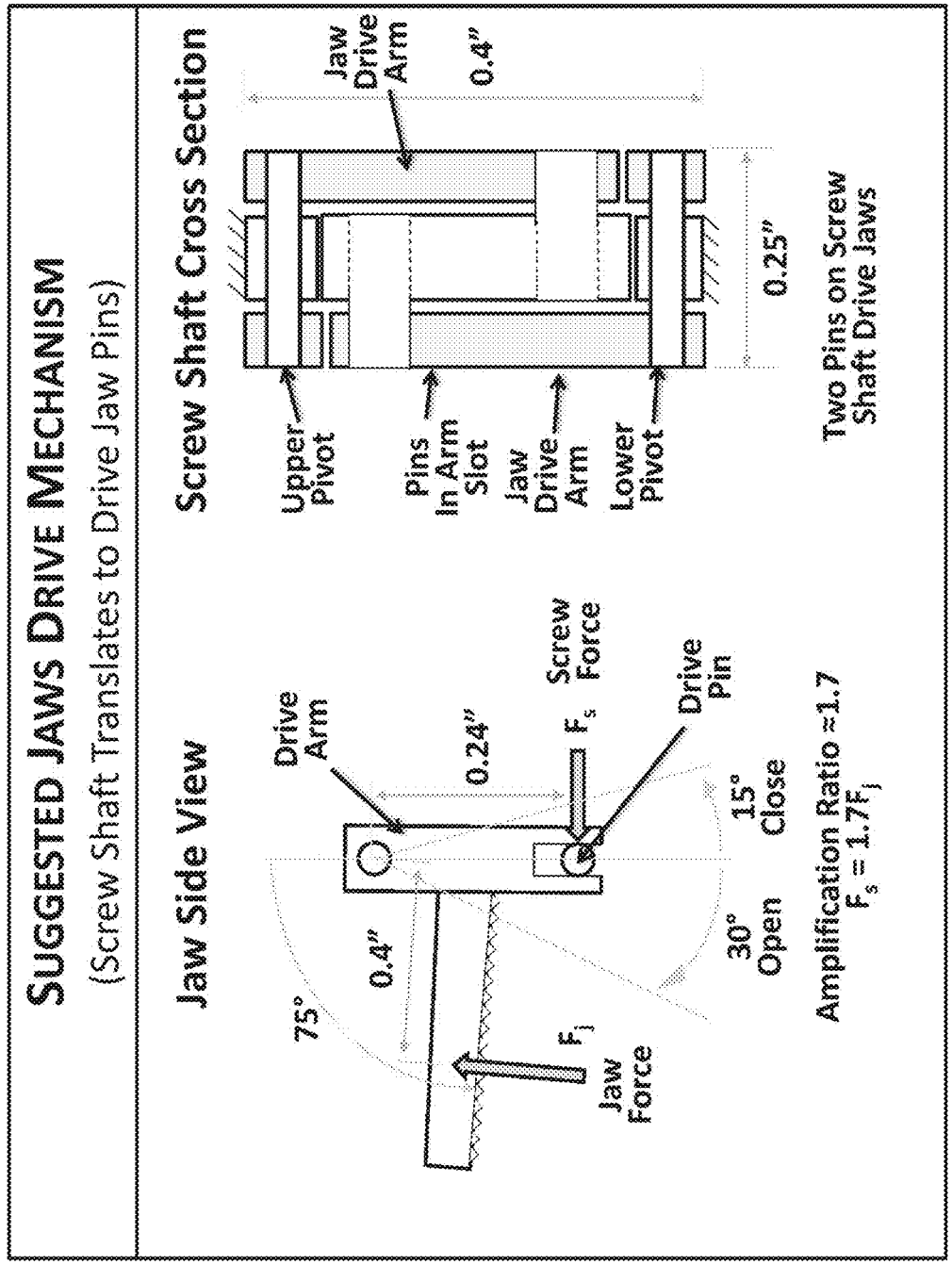
FIG. 4 is an illustration of an embodiment of a drive mechanism in which a screw shaft translates to drive jaw pins.
Figure 5:
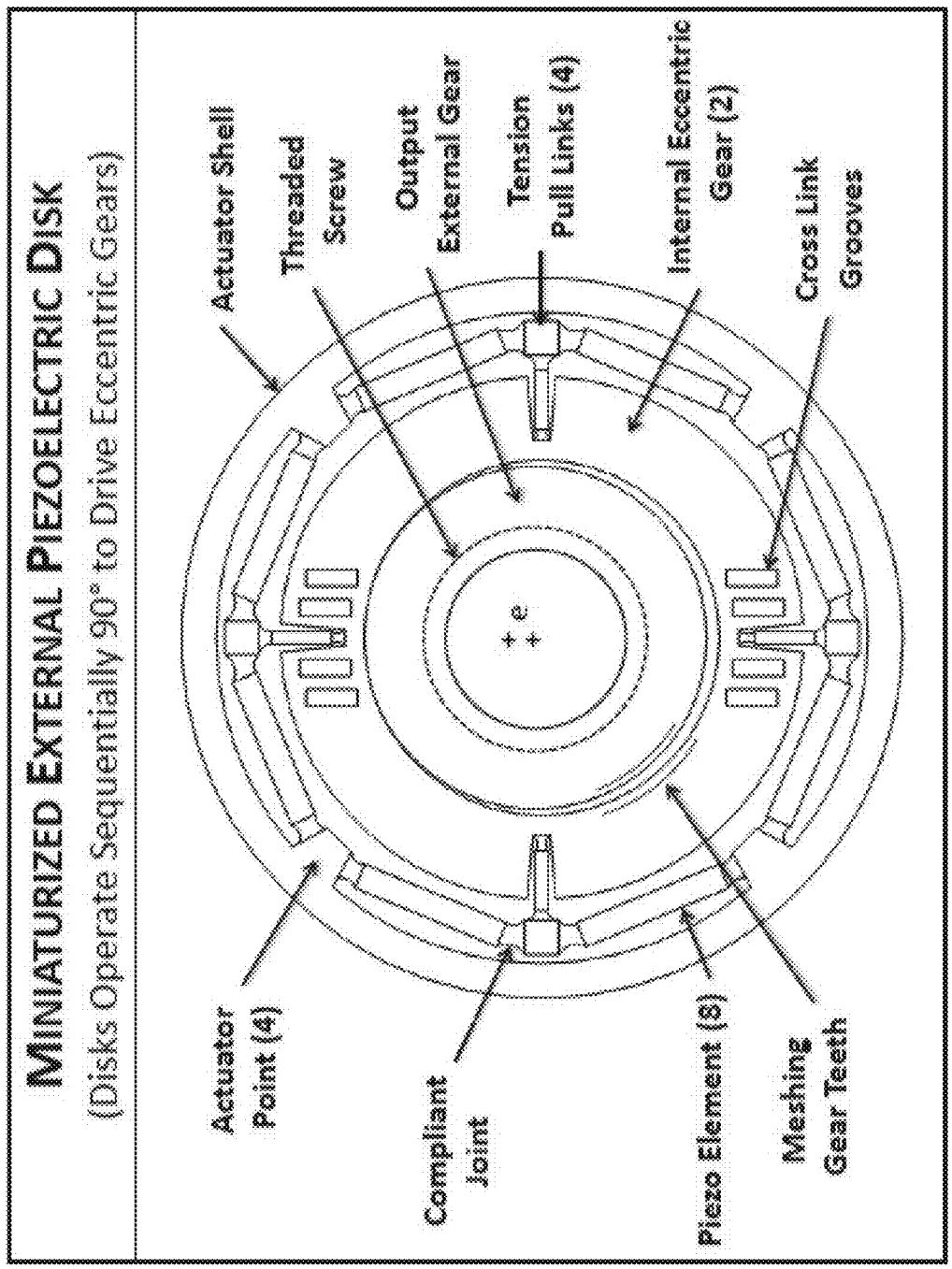
FIG. 5 is an illustration of an embodiment of a miniaturized external piezoelectric disk in which the disks operate sequentially at 90° to drive eccentric gears.
Figure 6:
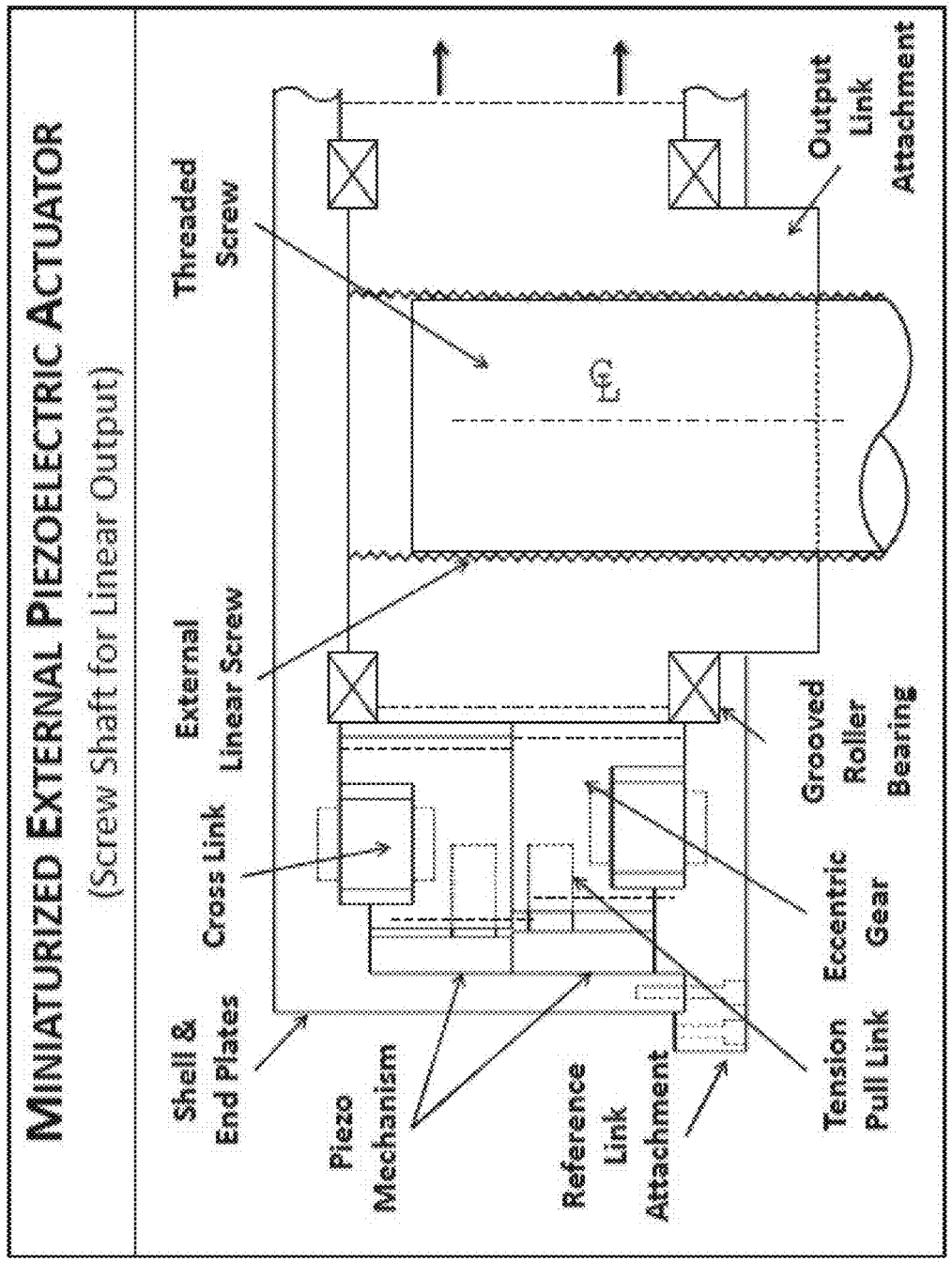
FIG. 6 is an illustration of an embodiment of a miniaturized external piezoelectric actuator equipped with a screw shaft for linear output.
Figure 7:
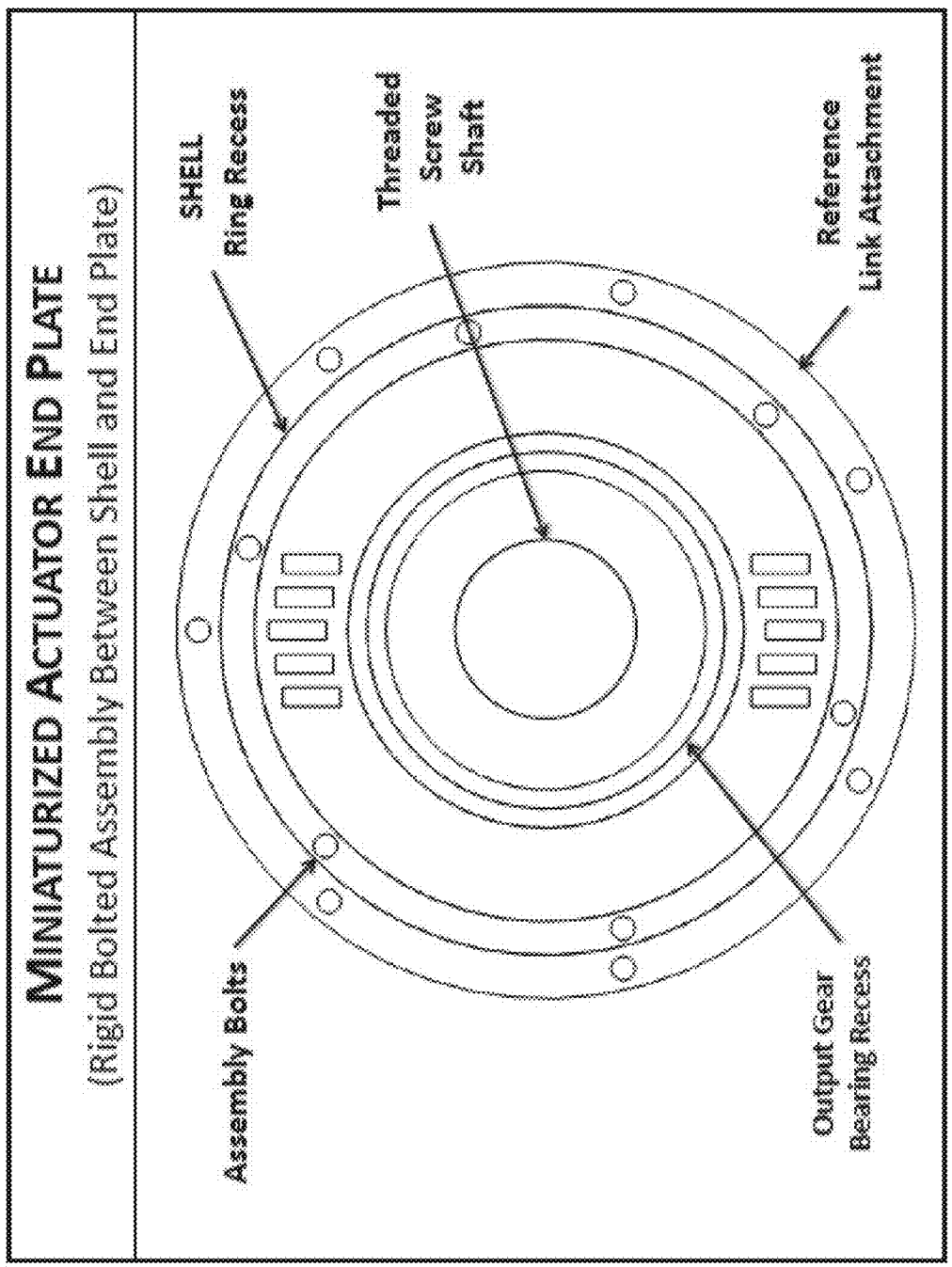
FIG. 7 is a miniaturized actuator end plate equipped with a rigid bolted assembly disposed between a shell and an end plate.

FIG. 4 provides more geometric detail for the gripper design. The average pin-to-pivot distance is 0.24", and that to the clamp force $F_j$ is about 0.4", to give the 1.7 ratio. The pair of parallel jaws constrains the rotation of the screw shaft (a relatively low torque value generated by friction on the screw threads). These jaws are anchored by pivots which rigidly hold the jaws parallel. Given the load on the slotted pins ($\approx 1.1 \times 1.7 \times 10 \times 2=37$ lbs.), it is seen that a large force must be generated by A1 on the drive screw. The actuator A1 in the embodiment depicted is designed for normal torque of 40 oz-in. and a peak torque of approximately 100 oz-in. The output screw shaft may have a 10-to-1 lead. This arrangement generates the necessary screw shaft force of 37 lb. to create a clamping force of 10 lb.

FIGS. 5-8 show the layout of the A1 actuator, which is a piezoelectric driven SPE modified with a 10-to-1 lead output screw shaft. In this case, the use of special grooved roller bearings are preferred to carry this high screw shaft load.

Actuators 2 and 3 create the equivalent of a roll/pitch universal joint to generate desirable spherical motion for the gripper. The total length from the jaw force $F_j$ to the pitch actuator A3 center line is 1.6" in the particular embodiment depicted. A3 is also a piezoelectric SPE. Given a lateral load at the gripper of 2.5 lb., this results in 64 oz-in. torque, which is above the design torque of 40 oz-in. Given a lateral load of 4.0 lb., the A3 torque would be 102 oz-in., which is equivalent to its peak torque level. These are large numbers, but the duty cycle for these class loads is modest. Also given intelligence (to assist the surgeon), this lateral force direction may be made to be collinear with the axis of A3, which would result in no applied torque about its output axis. Doing so would also result in no torque on actuator A2. Hence, intelligent software may be utilized to assist the surgeon to put the least torque demand on the wrist actuators to improve temperature control and their endurance.

The F/T (Force/Torque) sensor is considered as part of the wrist sensing system. With a lateral force of 2.5 lb. and an offset distance of 1.8", the moment would be 72.0 oz.-in. (0.4 ft·lb.). Given a lateral load of 4.0 lb. would result in a moment of 115 oz-in. (0.60 ft·lb.), which may be considered demanding. The maximum force along the F/T sensor center line would then be 4.0 lb.

Figure 8:
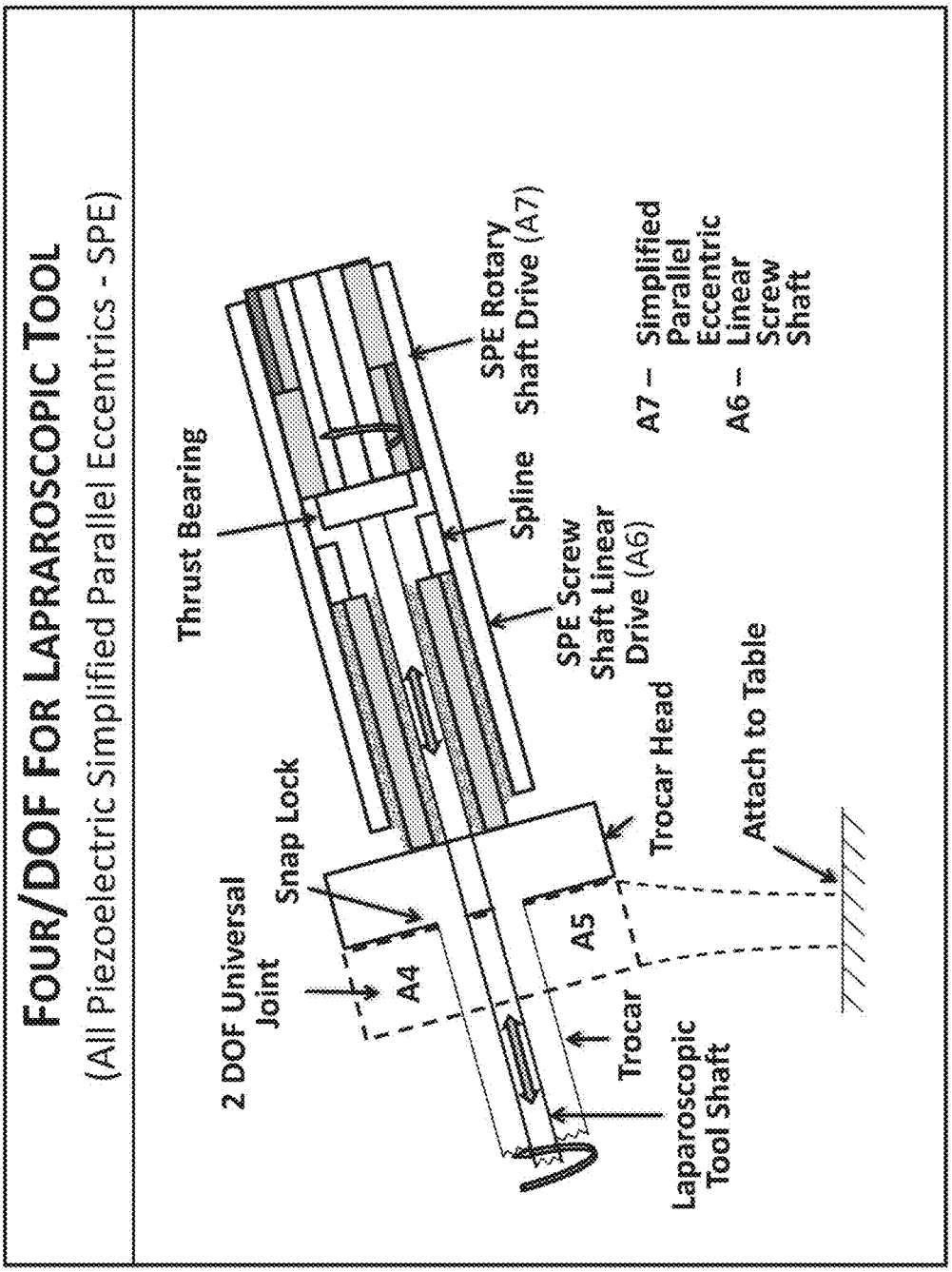
FIG. 8 is a four degrees of freedom laparoscopic tool equipped with piezoelectric simplified parallel eccentrics (SPEs).
Figure 9:
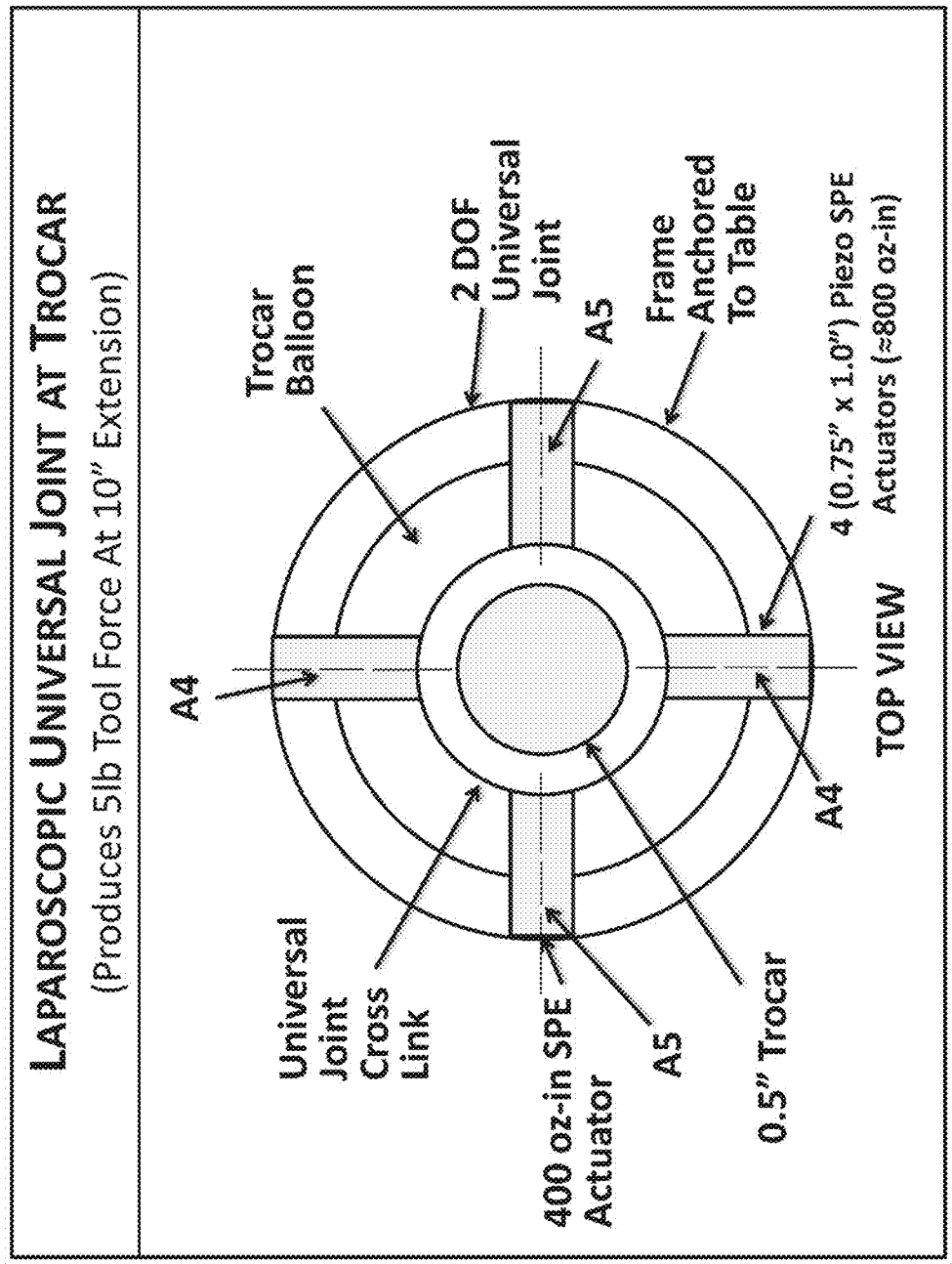
FIG. 9 is an illustration of a laparoscopic universal joint in a trocar.

FIG. 1 shows the layout of actuators A4-A7 in the external structure for the laparoscope manipulator. FIGS. 8-9 provide more detail for that arrangement. The 2 DOF universal joint with four actuators (2A4, 2A5) provides a balanced torque to carry the load at the end of the manipulator. With an A4, A5 size of 0.75" in diameter and a length of 1.0", the estimated design torque would be 400 oz-in. or a total axial design torque of 800 oz-in. Given a manipulator length of 10", this would enable a lateral force of 80 oz. (5.0 lb.) or a peak lateral load of 12.5 lb., which exceeds the maximum design (peak) loads on pitch actuator A3 by a factor of 2. This universal joint is mechanically anchored to the operating table to act as a position/force reference for the laparoscopic manipulator.

A6 is a piezoelectric SPE-driven screw shaft. It translates the laparoscope's shank in and out of the trocar. The output screw shaft does not rotate independently, since actuator A7 rotates this shaft to provide the last 2 DOF of the manipulator. A7 is a piezoelectric driven SPE. A7 is splined to the outer shell of A6, so that A7 translates with the in-and-out motion of the manipulator shank. These actuators have a lot in common with those found in handheld endodontic and surgical tools.

Figure 10:
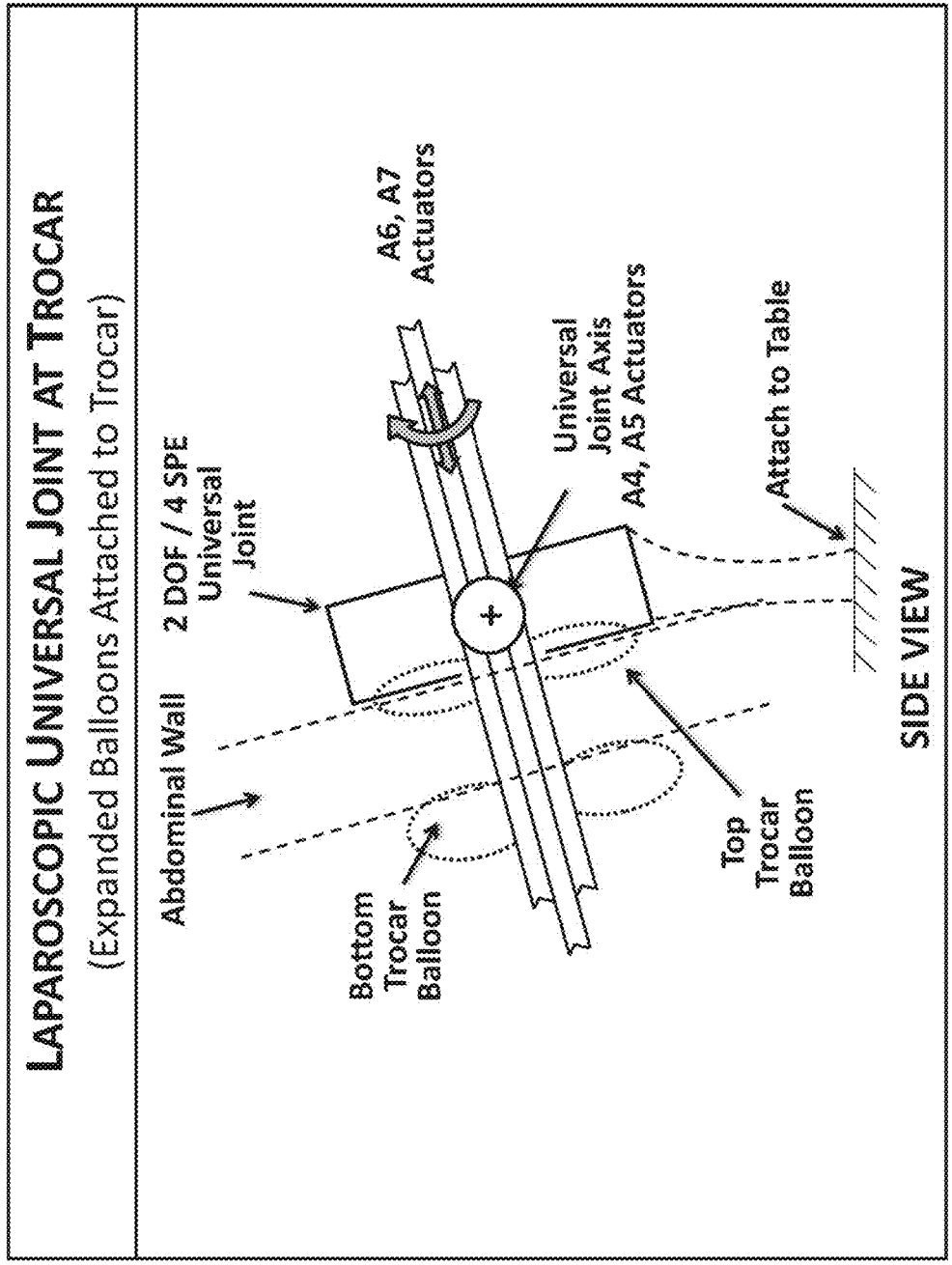
FIG. 10 is an illustration of a laparoscopic universal joint in a trocar equipped with expanded balloons attached to the trocar.

Finally, FIG. 10 suggests the use of trocar balloons on the inside and outside of the abdominal wall to put less stress on the incision and to give a better body reference for the laparoscopic manipulator. Each balloon is attached to the lower part of the trocar. The upper part of the trocar (the two parts snap together) is attached rigidly through the center of the cross link in the universal joint. The head of the trocar then is an integrated part of the overall design of the laparoscopic manipulator.

In the summary section provided herein, a representative list of 14 recommendations was provided that would guide the proposed development. TABLE 1 below illustrates how this laparoscopic manipulator moves the tech base in each mentioned direction with an estimate of how close each goal is achieved.

TABLE 1

Compliance of Proposed Laparoscopic Manipulator With Recommended Criteria

| | | |
|---|---|---|
| 1 | High | Cable drive manipulators have inherent movement latency because of accuracy friction on the pulleys and cables. Here, each of the piezo driven SPE (80%) actuators exhibit very little friction and directly drive their connected joint for a very high positional resolution. |
| 2 | Visual | These higher quality actuators and greater dexterity should enhance visual feedback scene acquisition. What is really needed is performance map visualization (20%) to the surgeon to guide them to system performance sweet spots. This SPE actuator technology moves partially (50%) in that direction. |
| 3 | Force | The F/T sensor at the gripper has a high potential to assist tactile feedback to the surgeon. Local actuator torque sensing would also (40%) have value. |
| 4 | Smaller | The high torque density of the SPE actuators gets the device very close to the lightweight (80%) ultimate goal. The estimated weight of the manipulator is 5 lbs. |
| 5 | Lower | Here, the cost should be 1/3 of the cost of the Da Vinci device in the prior art. Cost is expected to come down further with the quantity production of (40%) minimum sets of the SPE actuators with standardized interfaces. |
| 6 | High Force | The SPE actuators are remarkably torque dense and should work at levels (60%) with very high surgical task force levels. |
| 7 | High | The SPE actuators have no rolling element bearing in the load stiffness path, and virtually no torsion or bending elements, and thus result in (70%) exceptional stiffness. |

TABLE 1-continued

Compliance of Proposed Laparoscopic Manipulator With Recommended Criteria

| | | |
|---|---|---|
| 8 | Plug-and-Play | The SPE actuators are self-contained modules, such that play (30%) modularity with standardized interfaces may be readily achieved. |
| 9 | Archive | Good SPE position awareness from computer commands, operational (30%) F/T sensing combined with visual scene records permits useful storage of good/bad results of all operations. |
| 10 | Lessons | Application of predictive analytics to the archived data may yield comparative learned numerical evaluation of important parts of the operation for training (10%) purposes, to assist the practiced surgeon with operational criteria, and to assist the designer on what design refinements should be considered. |
| 11 | Minimum | This laparoscopic manipulator has been built of SPE actuator component modules both at the wrist and at the trocar. All modules may now be certified and designed in minimum sets to continuously (20%) improve performance and to reduce production cost. |
| 12 | Low Cost | Sensors provide data in real time (msec.) to make effective sensors decision making to augment the surgeon's commands. The F/T (30%) sensor at the wrist is especially important, but sensors at the actuators outside of the Trocar are also important. |
| 13 | Master | BLDC-driven SPE actuators in a 6 DOF master controller that are electronically backdrivable are important form providing a valid/useful master (20%) controller. |
| 14 | MRI | The piezoelectric drives eliminate magnetic fields in usual brushless compatible D.C. motors. The use of careful selected non-magnetic materials (aluminum, (60%) ceramics, plastics, stainless steel) may complete the laparoscopic manipulator. |

Miniaturized Actuator Tech Base to Support Surgical Laparoscopic Surgery

The systems and methodologies disclosed herein may also be applied to the development of a miniaturized actuator to drive wheels and manipulator arms on mobile cubesats for cost-effective exploration of space object surfaces. This tech base must support an improvement of 3 orders of magnitude over the best SOA in terms of torque, efficiency and volume.

Miniaturized actuators are required in numerous applications (such as, for example, surgical tools and robots, instruments, small hovercraft, social media cameras, and vehicles). Cost is a driver on Earth as it is in space, but the ratio may be 3 to 4 orders of magnitude higher (i.e., $100 vs. $100,000) for space applications. Considerable progress has been made in the last two decades on high frequency piezoelectric friction drives permitting high resolution, low force levels, but very poor efficiency (<10%). The driving force is rarely combined with a mechanical force amplifier such as a gear train. Amplification ratios of 100 to 200× are required to make these useful for anything but the least demanding output torque levels. The gear train that is normally used is a serial epicyclic gear train. However, such gear trains are characterized by considerable backlash, multiple bearings and gears, and considerable inertia, none of which are desirable in many applications.

Alternate prime movers are miniaturized coreless D.C. motors, which continue to be improved upon. Significant improvement in torque density is not expected. The present principal issue is accurate control over position and angular velocity. Fortunately, efficiency of 50% may be expected. At this scale, low efficiency suggests heat build-up with the threat of higher operating temperatures.

Three commercial miniaturized actuators are currently on the market. These are set forth in TABLE 2.

TABLE 2

Commercial Miniaturized Actuators On The Market

| Actuator | Description |
|---|---|
| Piezo Leg | Uses an epicyclic gear train driven by a piezo friction motor producing 2.13 oz-in. torque in a 0.68" diameter by 1.47" long cylinder. |
| Newscale | Uses an NTAF friction motor (from Austria) to generate 0.425 oz-in. in a 0.12" × 0.173" × 0.173" volume. |
| Precision Microdrives | Uses a d.c. motor driving an epicyclic gear train to produce 1.42 oz-in. of torque in a 0.4" diameter and a length of 0.8". |

These actuators have been compared with the miniaturized Piezo SPE actuators described herein which produce 42 oz-in. torque at 90% efficiency and a volume of 0.4" cube. The performance ratio comparison then becomes:

TABLE 3

| | Inverse | Direct |
|---|---|---|
| Piezo SPE | 1.0 | 1.0 |
| Precision Microdrives | 0.0017 | 588 |
| Newscale | 0.00022 | 4545 |
| Piezo Leg | 0.0000078 | 128,205 |

Of course, these numbers are approximations, but they suggests that the Piezo SPE, in terms of these three factors, beats the best existing technology by a remarkable 3 orders of magnitude. Other issues of ruggedness, durability, repeatability, and accuracy may all put the Piezo SPEs in a stronger position.

Initially, it may be desirable in some applications to use the Newscale prime mover to drive the SPE gear train. Except for the issue of energy loss due to high friction, this may be a useful short-term solution. The preferred embodiment of the SPE uses two miniaturized bearings (not in the load path). These two large-diameter, small cross-section bearings act as principal bearings rigidly holding the output internal gear relative to two stationary end-plates, and providing a high force capability in all six directions. These bearings come from several suppliers (for example, Timken). Each SPE gear train consists primarily of two external eccentric gears, two end-plates, and two cross links between the eccentric gears and the end plates. The output ring contains an internal gear which meshes with the eccentric gear (two tooth meshes, each of 3 to 6 teeth, 180° out of phase). These gears may provide a reduction ratio of 100-to-1.

One issue is nano-manufacture of the gear teeth and the tongue/groove elements in the eccentric gears, the cross links, and the end plates. A first-level analysis shows that these contact surfaces would experience a contact stress level of ≈6000 psi under the design load of 42 oz-in. if 3 parallel tongue/grooves are used on each side of the crankshaft. This contact stress goes down to 3600 psi if 5 parallel tongue/grooves are used; this stress level is considered quite modest. Of course, the sliding motion under load will create friction, but the stroke lengths are very short so that the energy loss will not be great.

Ultimately, the prime movers should become piezo linkage amplifiers to efficiently create a precision driving force/torque on the eccentric gear. These linkages have necked-down sections to permit small levels of relative rotation without backlash (i.e., a flexible linkage structure). The 4 piezo drivers for each eccentric gear may be energized sequentially to create a rotating force (as if it were a mechanical eccentric). This sequence may be thought of as a stepping motor; i.e., the steps are commanded one at a time, so the system quickly responds to command with no uncertainty and virtually no wasted energy.

Miniaturized Piezoelectric Parallel Eccentric

Torque dense, precision, and rugged miniaturized actuators (⅜" to 1" in diameter) may be designed based on the teachings herein and using the best principles of mechanical design driven by proven piezo-electric elements. Such actuators will preferably use compliant linkage amplifiers (12 to 1) to create eccentric motions for two parallel gears which oscillate without rotation (180° out of phase and perfectly balanced) to drive either an internal (large diameter) or an external (smaller diameter) gear as the actuator output. These actuators do not require any rolling element bearings (for simplicity at these very small scales) and may utilize a dry lubricant (likely graphite). Also, all components would be non-magnetic to be translucent to magnetic imaging waves.

A large community of designers are working on miniaturized actuators, usually driven by various "smart" materials (such as, for example, shape memory alloys, piezo-electrics, and electro-magnetostrictive alloys). Japan has long led this field with remarkable results for MEMS. Because of the drive for social media, miniaturized actuators are now being developed for small cameras, very small valves (for human body inserts), small earpieces, and the like. The need for miniaturization of actuators exists for use in defense systems (miniaturized UAVs), small spacecraft, manufacturing cells (small cells to make micro-electronics), automobiles (fuel valves), and certainly in dexterous surgical devices (robots, surgical tools) to operate in the human body.

In the past, piezoelectric drivers were used to drive compliant linkage amplifiers to move a friction pad using high frequency (150,000 Hz) piezoelectric (ultrasonic) motors against a drum to form a rotary motor to drive a set of reduction gears. These devices may be made quite small, operate with notable smoothness, are backdrivable, and provide a modest torque density. Many of these devices are linear, although several rotary actuators have been developed recently. The main weakness in all this development is the maintenance of precision under significant load variations, which is essential to carry out important physical tasks under human command (as in surgery). To address this weakness, a device is proposed herein that employs hypo-cyclic motion (a wobble gear which contains two gears with external teeth) to mesh with a stationary internal gear (part of the shell) and a second rotating internal gear as the actuator output. The piezoelectric motion amplifiers cause the wobble gear to oscillate with rotation to drive the output gear at a high reduction ratio (say, 100 up to 1000-to-1). This unit may carry a very high output torque for its scale. Unfortunately, the wobble gear must rotate at, say, 3000 RPM to provide an output speed of 30 RPM. This suggests a need for balancing, and a high need for well-lubricated rolling element bearings, all of which are difficult to achieve at very small scales.

Parallel eccentric gear trains have been developed by the present inventor which are driven by electric prime movers (BDC, SRMs). These prime movers drive a crankshaft with two eccentrics to oscillate the parallel gears (180° out of phase and perfectly balanced) which, together, drive an internal output gear. Recently, that work has reduced the number of rolling element bearings from 16 to 6 using an Oldham crosslink with tongue and grooves to prevent the rotation of the eccentric gears. This simplicity may depend on quality lubrication of the cross link tongue and grooves (perhaps at 6,000 CPM) which oscillate with a motion range of perhaps ⅜".

It is proposed herein to use piezoelectric elements with compliant linkage amplifiers to be the prime movers of the parallel eccentric gears which will be driven to oscillate (without rotation) 180° out of phase, thus resulting in perfect dynamic balance at all cyclic speeds. In a preferred embodiment of such a device, there will not be any rolling element bearings. Moreover, the piezo electric elements will be as long as possible to result in reasonably sized oscillations in the parallel gears. This may allow the use of gear teeth of sufficient size to enable significant load capacity (much higher torque density than is now available at this scale of actuator). This is partially due to the pair of tooth meshes 180° out of phase. The Oldham crosslinks and joint bearing sliding surfaces may use proven dry lubricants (such as, for example, graphite), which usually yields a friction coefficient near 0.1 (or, 10%). Note that the duty cycle for these miniature actuators will not be very demanding, with peak loads/velocities occurring infrequently. Hence, power losses and resulting rise in temperature is not expected to be an issue.

Figure 11:
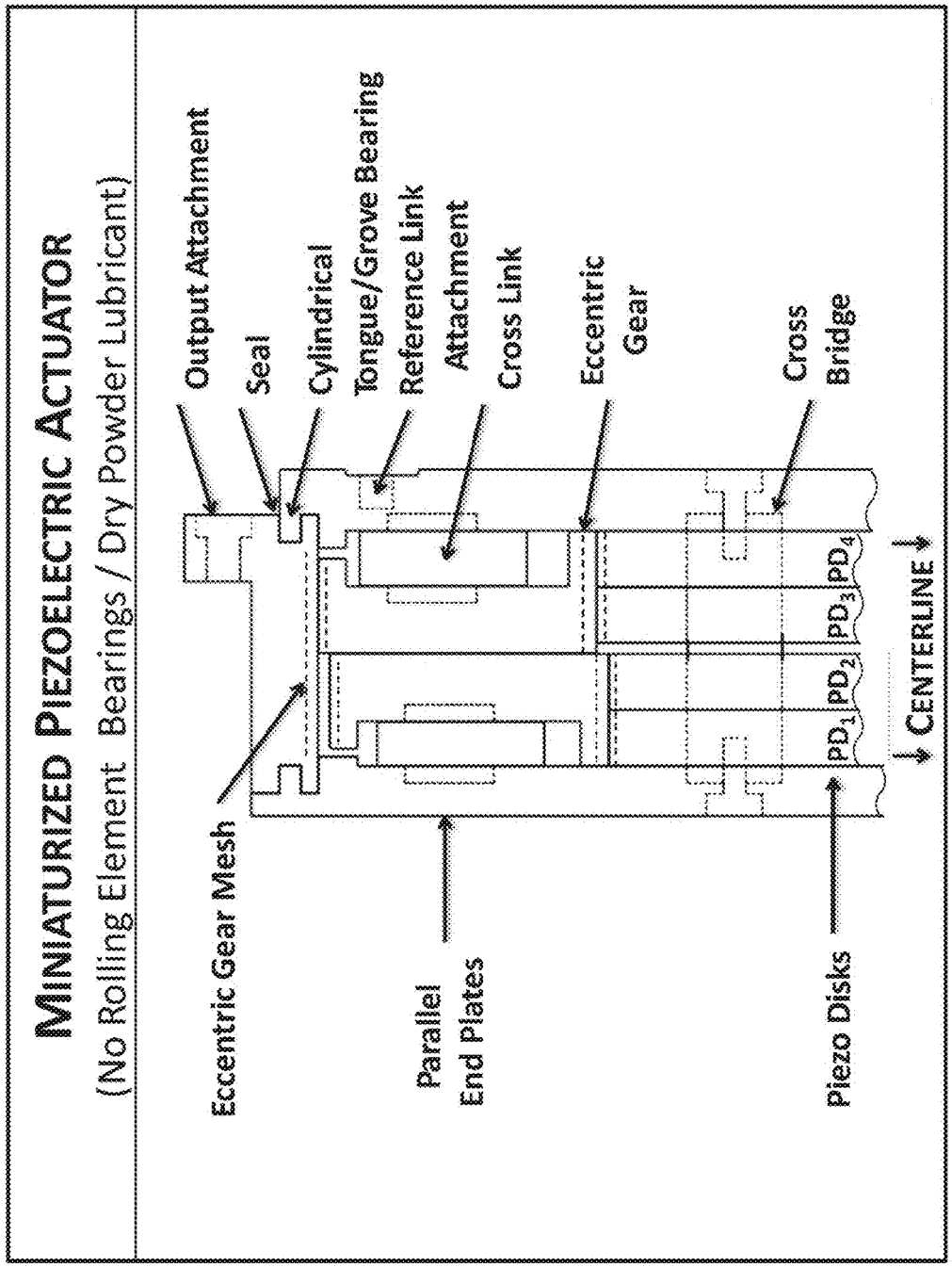
FIG. 11 is an illustration of a miniaturized piezoelectric actuator.

FIG. 11 shows the layout of the actuator where the piezo drivers are internal to the parallel eccentric gear/Oldham cross link assembly. The two end plates constrain the output internal gear using two widely spaced cylindrical tongue and groove sliding bearings to result in exceptional rigidity. In this case, the eccentric gears are external to use 2 meshes (180° out of phase) to drive the output gear. The end-plates are equipped with grooves to constrain the rotation of two cross links. The crosslinks, in turn, are equipped with tongues on both sides to permit the eccentric gears to oscillate without rotation.

Figure 12:
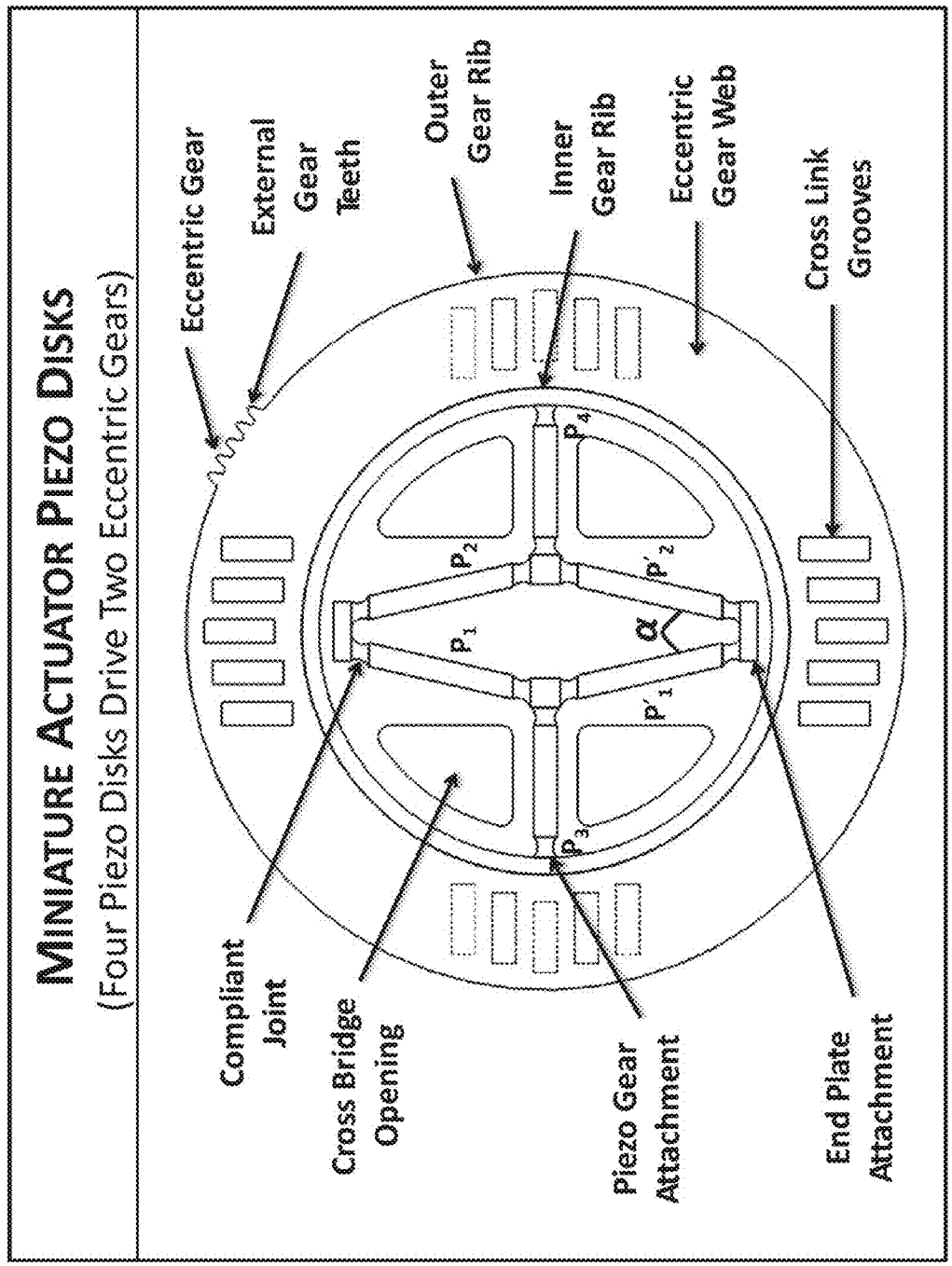
FIG. 12 is a side view of a piezo disk which may be used in the actuator of FIG. 11.

FIG. 12 is a plan view of one of the eccentric gears driven by a set of 6 equal length piezo elements. These assemblies are referred to herein as piezo disks (PDs), of which, there are 4 for the actuator. Piezo elements P1P1' and P2 P2' form a compliant linkage amplifier (12 to 1) to drive a third piezo element P3 (or P4) to drive the parallel gears 180° out of phase. Piezo disk PD2 performs the same function 90° out of phase to result in four motions in 90° increments.

Each compliant mechanism preferably utilizes necked-down sections to be small motion pivots of high stiffness and no backlash. For example, if the piezo elements are 0.5" long and yield "a stroke of 0.001", then all three elements in the amplifier would yield an output stroke of 0.013" and a tooth height of 0.010" or 0.012". Given a gear of 1.5" in diameter, the number of teeth could be 100 or a tooth thickness of 0.022" and a width of ⅛". With two meshes using a stress level of 25,000 psi, this may result in a driving torque of about 5000 oz.-in., which is quite large for this size of actuator. Reducing the scale by 2× would result in about 625 oz.-in. and to ⅜" may yield a very useful torque of 78 oz.-in. or a force of 25 oz. at a 3 in. radius. It is expected that normal operating loads would be 40% of these design values. Note that this actuator would be fully responsive to human command at a wide range of velocities in order to meet complex duty cycles.

Figure 13:
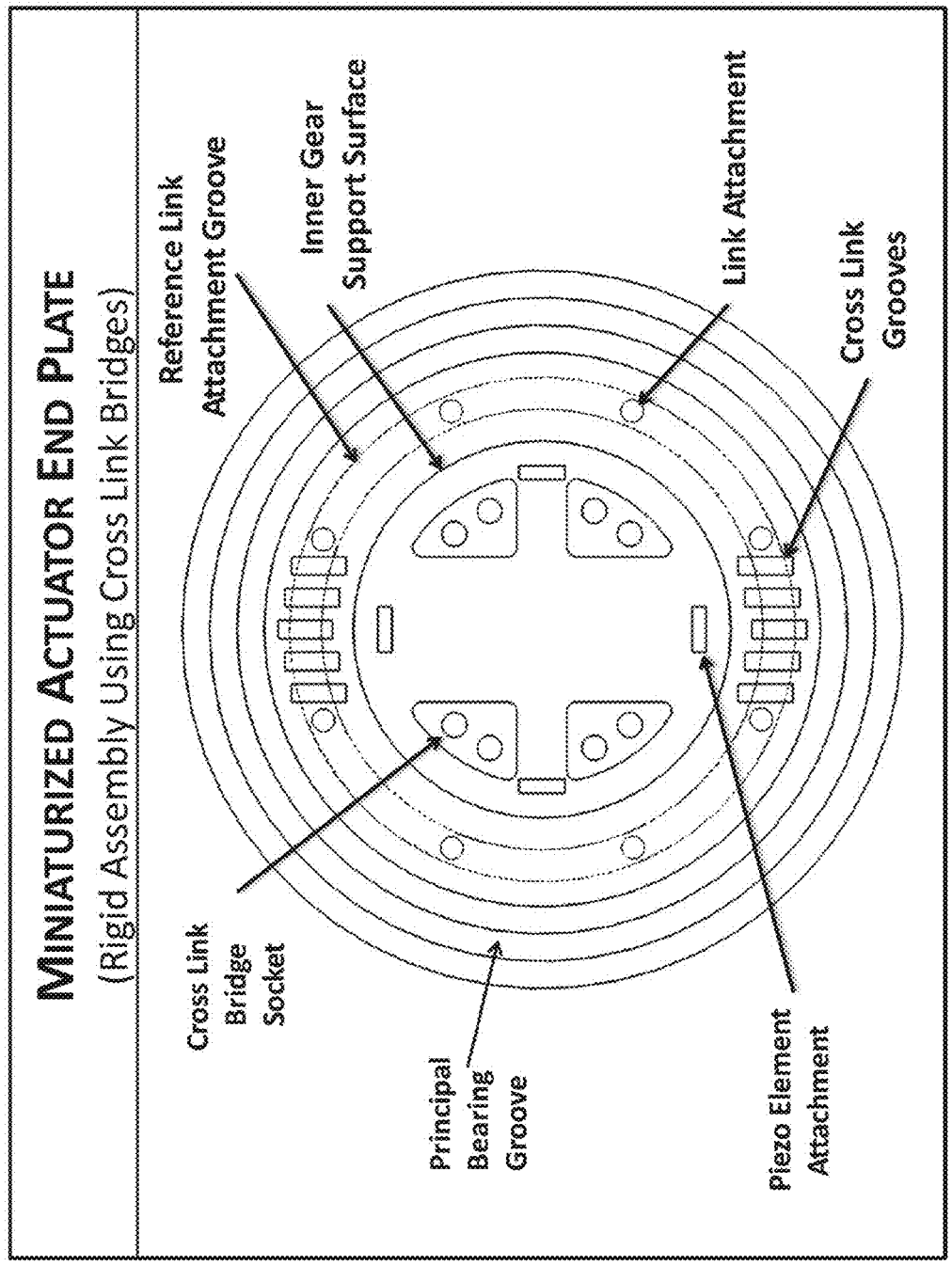
FIG. 13 is a side view of an end plate which may be used in the actuator of FIG. 11.
Figure 14:
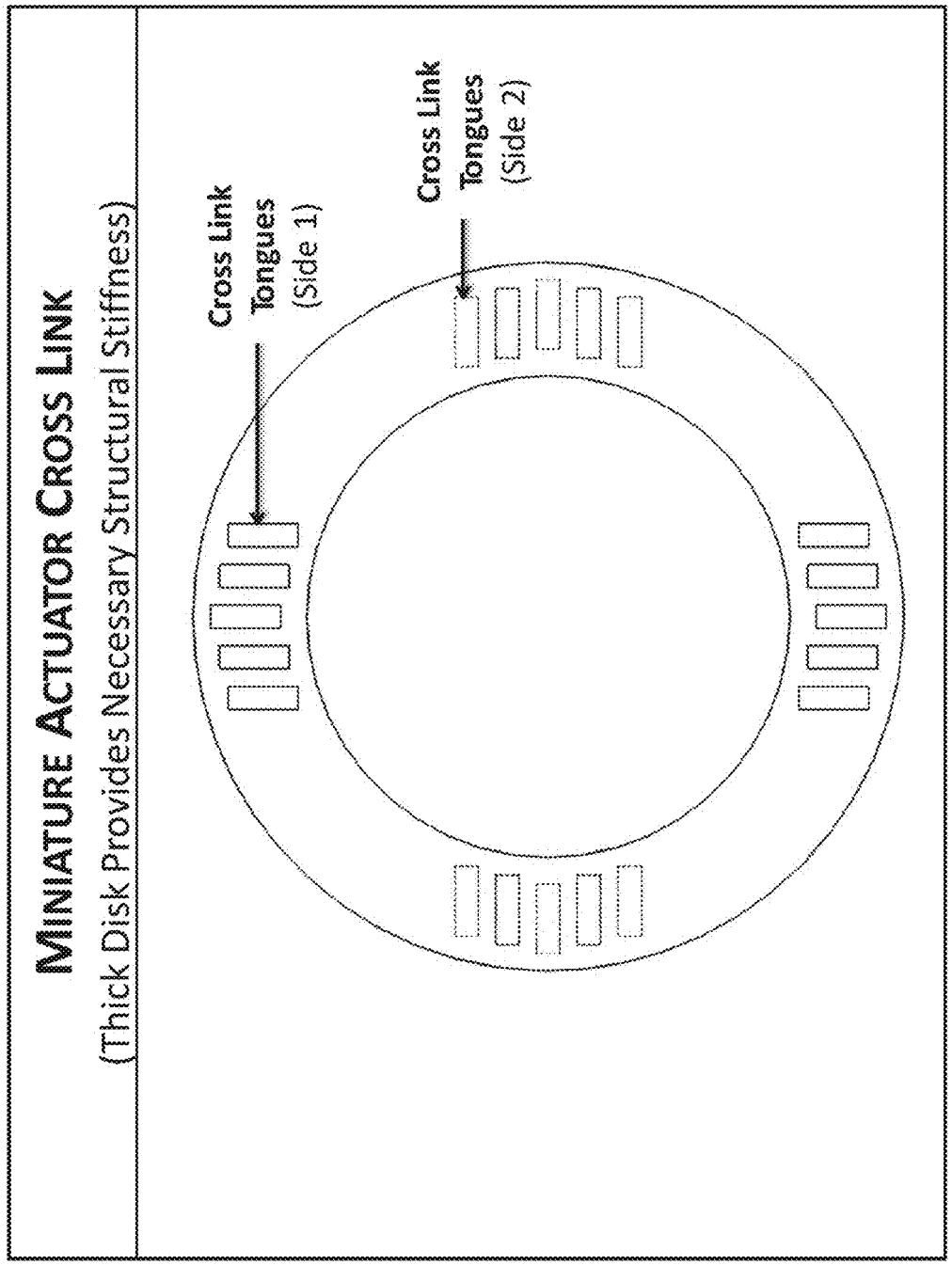
FIG. 14 is a side view of a cross link which may be used in the actuator of FIG. 11.

FIG. 13 shows the layout of one of the end plates, and FIG. 14 shows the cross links for this actuator. The end plates are joined by four cross bridges which enables the whole to be bolted together in a rigid structure. Both end plates provide cylindrical tongues to mate with two sets of grooves in the output gear to form the principal bearings for the actuator. These tongues could be designed as spaced jeweled wedges mating with spaced jeweled triangular grooves to reduce friction.

It should be noted that the two sets of piezo amplifiers operate 180° apart. This suggests that when one set is active (in compression), the other set would be put in tension unless the relaxing of the signal on the second set returns it to its un-energized configuration. If this becomes an issue, a small slider at the attachments for P3 and P4 may carry the compressive load (at a limit stop) and release the tension for the inactive piezo amplifier.

Figure 15:
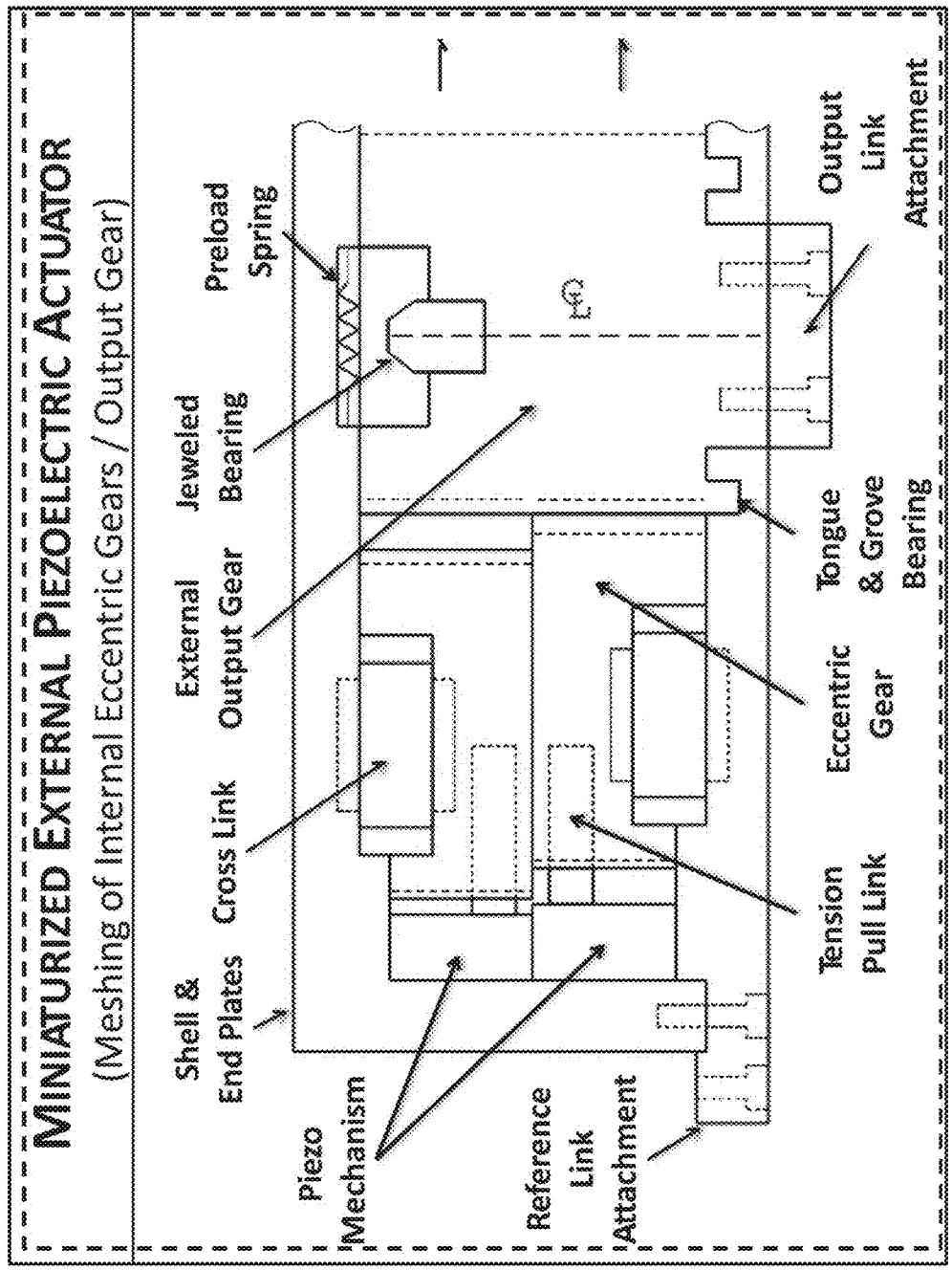
FIG. 15 is an illustration of a miniaturized external piezoelectric actuator.
Figure 16:
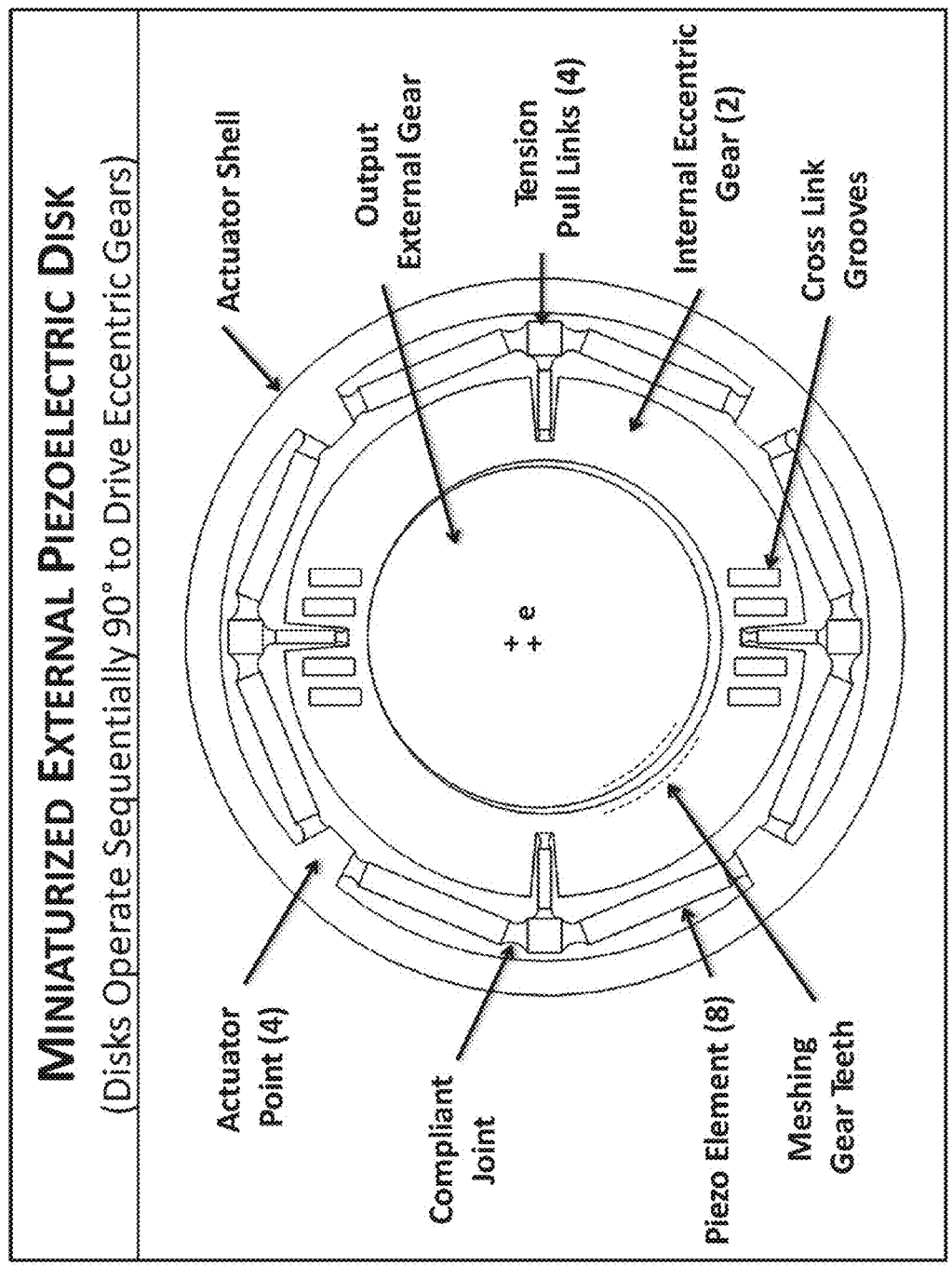
FIG. 16 is an illustration of a miniaturized external piezoelectric disk.

A second embodiment of a miniaturized actuator is shown in FIG. 15. This embodiment uses two piezo disks (one for each eccentric gear) that each utilize 8 piezo elements, each of length l, in 4 sequential compliant linkage mechanisms (see FIG. 16). These link mechanisms may yield a stroke length of 0.024 f. The output of the linkage amplifier uses a tension link to pull the eccentric gear towards the outside of the actuator shell. The cross link serves the same purpose as an Oldham coupling to prevent the eccentric gear from rotation.

In this case, the parallel eccentric gears are internal to mesh with a central external gear as the output for the actuator. This results in an eccentric motion of e≈0.02 f. Note that placing the piezo elements far from the centerline maximizes their length l. Preferably, the linkage amplifier uses compliant pivots throughout.

Figure 17:
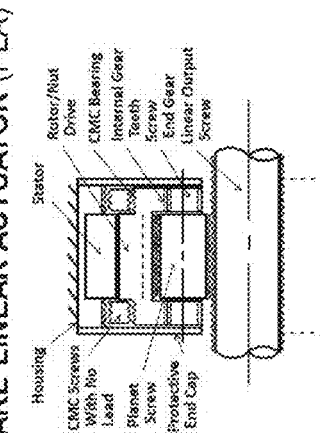
FIG. 17 is an illustration of a pancake motor/nut drive for a planetary screw.

One of the principal bearings is a cylindrical tongue and groove attached to the output external gear and meshed with a groove in the end plate (see FIG. 17). The other principal bearing may be a spring preloaded jeweled bearing of good ruggedness and reduced friction. This arrangement of the miniature actuator permits continuous rotation so that it may be utilized as a rotating surgical tool or for any other similar function.

One reality of the necked down amplifier linkages is that they are very stiff and do not yield very much deformation under load. These amplifiers, then, would typically not allow the eccentric gears to oscillate unless a gap is made available at their support brackets on the end plates. When the teeth are fully engaged, the gap would open to the value e of the eccentric 180° opposite the tooth engagement. Also, at ±90° from the tooth engagement, the gap would be zero. This frees up the motion of the eccentric gears. Note that the gap closes very slowly (in ¼ turn) and does not represent a potential for shock induced vibrations.

Figure 18:
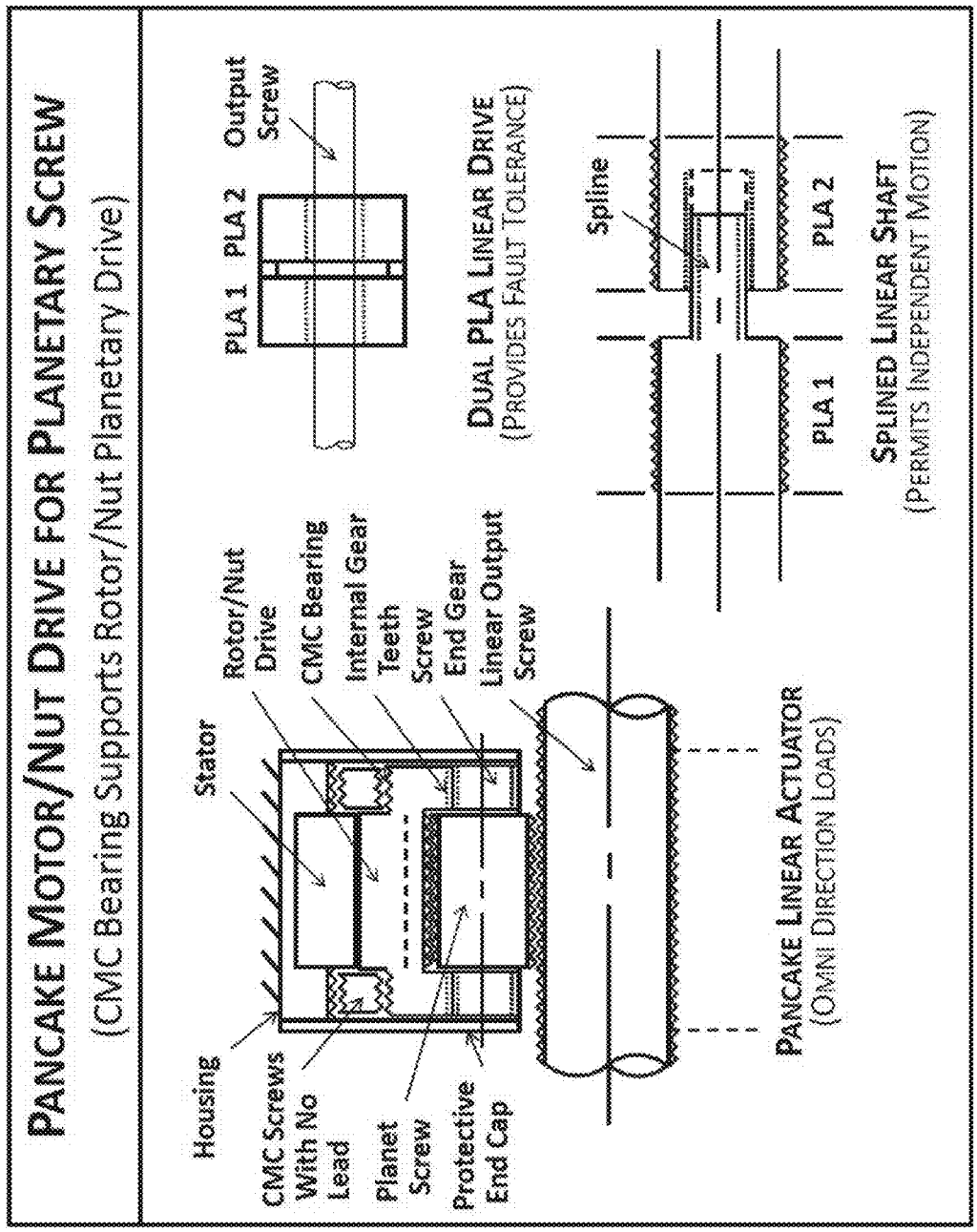
FIG. 18 is a pancake motor/nut drive for a planetary screw.

Because of the pancake shape of these miniaturized actuators, they can easily be assembled into a universal joint with two actuators on each axis to provide exceptional ruggedness and torque density (See FIG. 18). It appears that the external piezo drive actuator is best suited to this arrangement where the output gear is attached to the universal joint inner block cube.

Pancake Linear Actuator

Electro-mechanical actuators are disclosed herein which are of great simplicity and high force density (low weight and volume). This may be achieved by creating a pancake configuration with a central stator/rotor with their relative motion constrained by CMC's exceptional grooved roller bearing. The rotor in such a configuration acts as the nut of a rugged CMC planetary screw transmission to effectively carry a very high load.

Planetary screws have been manufactured for several decades by SKF and Rollvis, both of northern Europe. Recently, Creative Motion Control (CMC) has begun production in the U.S. It has been demonstrated that dual fault tolerant planetary drives for linear actuators are technically feasible. Unfortunately, they became rather complex and heavy, and fault tolerance was difficult to assure.

Heavy machinery (such as, for example excavators, loaders, mining and agricultural machines) usually use hydraulic actuators because of their high force density and simple on-off controls. Also, hydraulics tends to be lower cost at purchase, although they represent relatively high life-cycle cost (in terms of, for example, maintenance, hose leakage, and low durability). Architecturally, many designers would like to plug in an electro-mechanical actuator (EMA) without changing the basic geometry of their machine. The linear EMA may be much more durable, may substantially reduce maintenance, may be more efficient (by perhaps 3 to 5×), permit high resolution output control, be very responsive to command, and do so at higher effective force density. These benefits are very much sought after for aircraft, helicopters, drones, hovercraft, manufacturing, active vehicle suspensions, etc.

FIGS. 17-18 depict a particular, nonlimiting embodiment of a Pancake Linear Actuator (PLA). The central stator in this embodiment is attached to the reference frame of the PLA. The symmetric stator shell holds the internal grooved races for two CMC grooved roller bearings of exceptional load capacity in all force directions (perhaps 15× that of equivalent tapered roller bearings). These grooved rollers mesh with outer grooved races attached to the rotor of the motor. The rotor shell contains two symmetrical internal gears to drive a finite number of planetary screws (driven by the rotor screw threads), which in turn mesh with the primary threaded output shaft to move in the axial direction of that shaft. All components in this system are preferably symmetrically loaded, provide exceptional ruggedness and shock resistance, generate low friction for high efficiency, and provide high stiffness in all directions. Lost motion may be reduced by making the planetary screws ovoidal.

Duality of the PLA (which might be labeled DPLA) may make this actuator fault tolerant (see FIG. 18b). PL1 and PL2 outer shells are locked together (perhaps with spacers for better cooling) for the DPLA. Each must carry the same force, but their motion (velocities) add, so the total power of the DPLA may be split between the two PLAs. FIG. 18c shows that the linear screw output shaft may be split using a spline to permit the required relative linear motion. The whole unit may be jacketed to protect the screw threads and contain the lubricant. One of the limitations of the PLA is that the reduction ratio is restricted by the upper limit of the output screw lead of 10 to 1. The dual PLA provides a total of 20 to 1 by adding the displacements (velocities). I may also be used as a differencing mechanism (+/−), which may improve its resolution. In both cases, the load capacity remains the same for that of a single PLA. To solve this issue, a front end star compound gear train may be utilized to raise the reduction ratio to 100 to 1.

Advances in Intelligence and Motion Capability for Endodontic Instruments

The principles disclosed herein may be applied to endodontic instruments for dental root canal operations. The history in this field shows considerable manual dexterity gained after extensive training to control a combination of rotation/oscillation motion with associated force/torque values which embodies considerable trial and error judgment. In this application, voice commands may be utilized to set motion ranges and force levels at the tool by embedding two unique miniaturized actuators of high responsiveness, and to then provide the endodontist with visual map representations (of the root canal and the instrument's performance) of the full process as it proceeds, in real time.

Various advances have been made in the development of endodontic instruments. A significant breakthrough occurred with the use of nickel-titanium for the file because of its highly unusual elastic range of deformation. This allowed low force level conformation to root canal shapes (i.e., sharp canal turns). The material is easily formed/machined into a wide range of shapes with cutting edges/flutes in complex geometries. This complexity requires in-depth training by the endodontist where his "touch" must tell him everything, with some benefit from visual effects of irrigation and debris removal and timed radiographs. In general, the procedure is a combination of rotation (dominant) and oscillation (as needed). Generally, forward rotation with intermittent small back-steps appears very useful. Oscillation is used to assist irrigation and debris removal. There appears to be considerable judgment by the endodontist to make this work. Nonetheless, repeat canal reconstruction can take 2 to 2½ hours, which involves considerable expense in terms of personnel, equipment, and facilities. The systems and methodologies disclosed herein may be utilized to enhance the visual information supporting the endodontist's judgment, reduce procedure times, and lower costs.

Some instrument suppliers have provided powered instruments for combined rotation/oscillations with nominal choices in speed/motion ranges. Unfortunately, all of these efforts have a single actuator input (with 2 or 3 speed settings) with a fixed kinematic relationship between oscillation and rotation. Also, there appears to be inadequate feedback (force levels) to the endodontist except for touch awareness.

The Simplified Parallel Eccentric (SPE) provides a potential answer to these issues. The SPE contains a minimal set of parts and is ideal for rotary input to the file. Also, a miniaturized planetary screw transmission from Creative Motion Control (of Seattle, Wash.) may be driven by an external miniaturized D.C. motor. Both of these reducers permit controlled oscillations/rotations of a wide range of speeds/motion scales, start-stops, and other operations, all under voice command (such as, for example, slower/faster, backup/go forward, more/less rotation, more/less oscillation, more/less force) where the endodontist's judgment becomes the principal means to enhance the quality and speed of the procedure.

Figure 19:
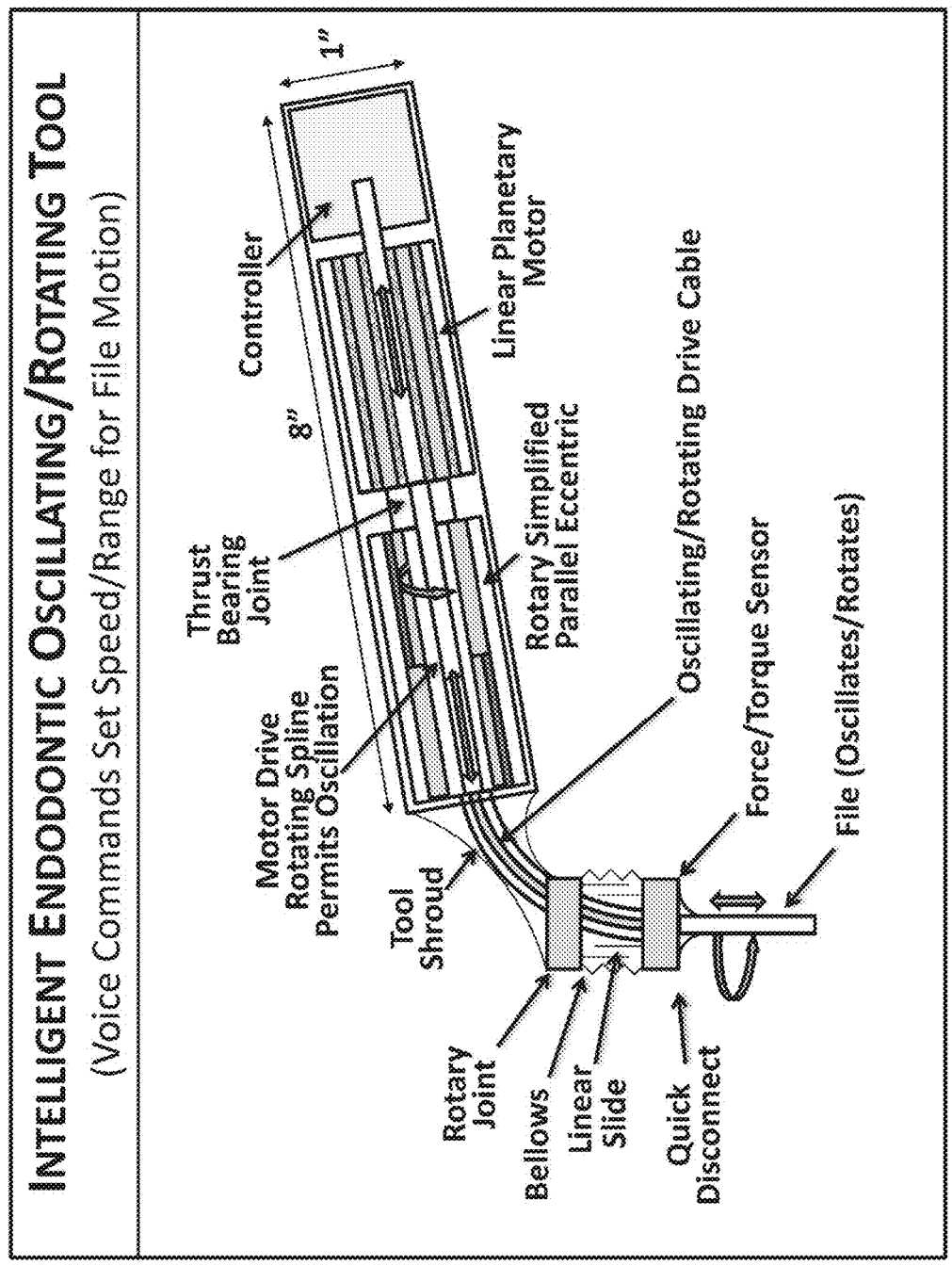
FIG. 19 is an intelligent endodontic oscillating/rotating tool.
Figure 20:
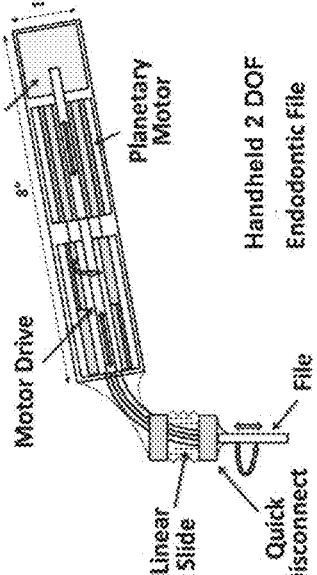
FIG. 20 is an illustration of some features of the endodontic tool of FIG. 19.
Figure 21:
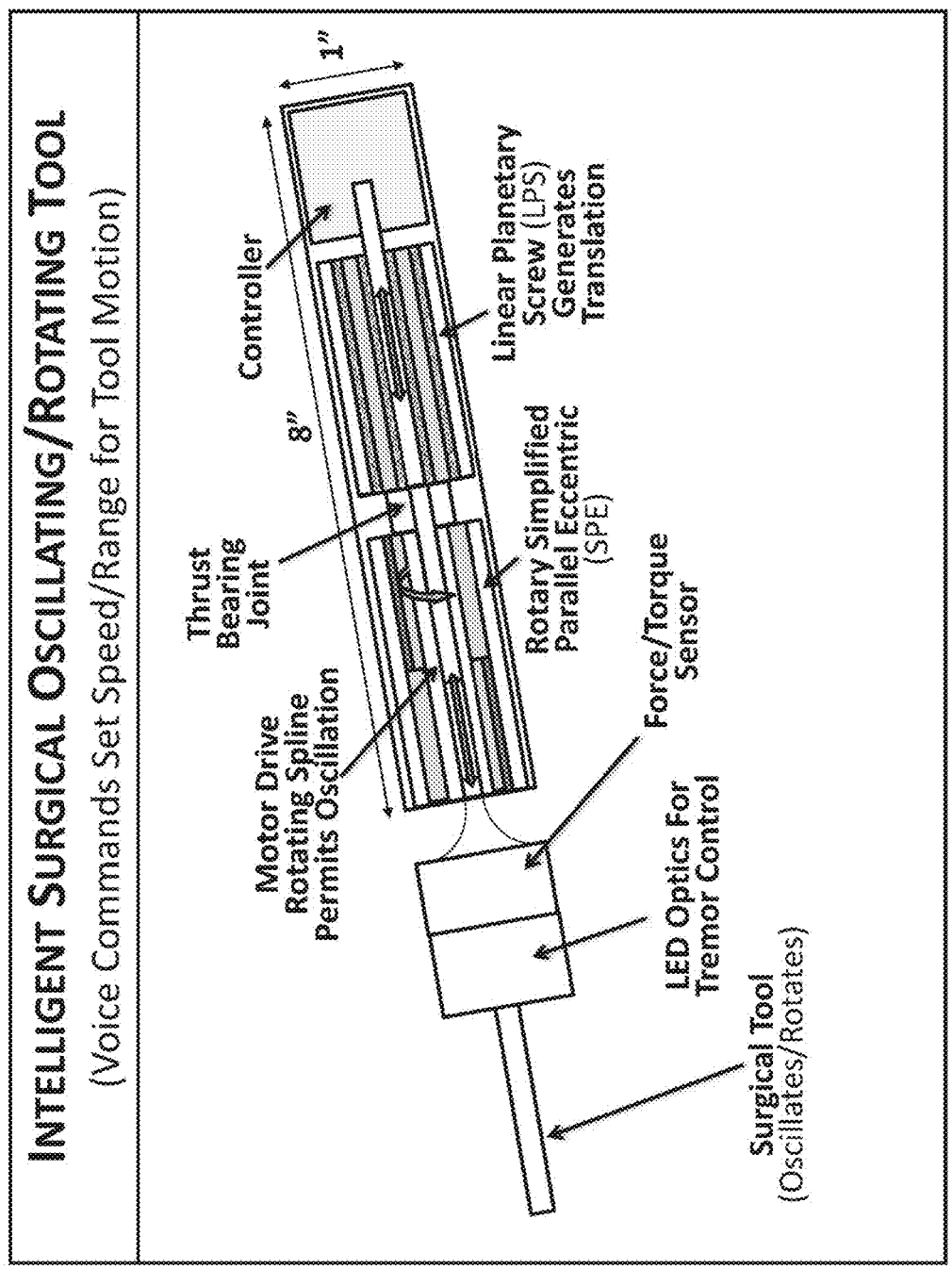
FIG. 21 is an illustration of an intelligent surgical oscillating/rotating tool which accepts voice commands to set the speed and range of tool motion.

FIGS. 19-21 depict a particular, nonlimiting embodiment of a hand-held endodontic instrument in accordance with the teachings herein. This instrument contains two unique actuators, a transmission coupling in the form of a rotating/oscillating drive screw/cable, an end-of-tool 2 DOF joint, and a force/torque sensor with a quick attachment to a file. The body of the tool is preferably at 60-70° from the vertical centerline of the file. This body contains the two actuators and their required controllers. The linear planetary screw/motor oscillates the output screw with an adjustable motion (adjustable in terms of, for example, range, speed, and start/stop). This output screw then oscillates a spline inside the second actuator, which rotates the spline with a similar adjustable motion. The rotating/oscillating spline is connected to a cable inside a curved fixed housing, which joins the tool actuators with the 2 DOF file joint. This small 2 DOF assembly drives the file which is attached with a quick-disconnect to a force/torque sensor.

Each actuator responds to complex commands in range, speed, force, acceleration, or other parameters, all under the voice command of the endodontist. All sensed information at the file and at the prime movers may be displayed as performance maps to enhance the judgment of the endodontist. All operations may be archived and analyzed for lessons-learned to refine human judgment (either in training or in practice). Lessons-learned may generate useful operational criteria and helpful data to enhance future tool design. All of this is called intelligence and is the basis for the Next Wave of Technology (NWT) for all intelligent machines (including, for example, vehicles, robot surgery, aircraft, construction machinery, and orthotics), especially where human judgment is the key.

A Concept for a 2 DOF Handheld Surgical Tool

In some embodiments of the surgical tools disclosed herein, two high performance piezoelectric (or BLDC) actuators may be utilized to drive 2 DOF for oscillation and rotation at the surgical tool for precise motion control under voice command of the surgeon. Using specialized F/T sensors, LED optics, inertial sensors, this system may largely filter tremors and reduce the effects of sudden impulses/jerks.

The fundamental sensor material for small scale sensors is polysilicon, which is quite stable to various environmental conditions (such as, for example, temperature, humidity and endurance). These sensors are preferably designed to survive radiation and sterilization. Sensor manufacture includes μEDM laser micro-machining, stereo lithography, and other such operations. Useful sensors include for example, temperature, pressure, and force sensors, as well as gyroscopes. A special emphasis has been placed on the Fiber-Bragg Grating (FBG), which measures axial strain. Needle insertion following a curved path in body tissue is typically achieved with a 2 DOF device (one translation and one rotation) where the stylet (holding the needle) has a permanent bend in its shaft so that, when it is rotated, it directs the needle to follow a curved path. Needle probes with multiple chambers are used to deliver in-situ drug treatments.

W. T. Latt (2011) describes a refined handheld tool, MICRON, first conceptualized in 2003, which reduces surgeon tremors and errors by 20 to 50%. It uses a rather cumbersome LED light ring which is intended to maintain a desired force level at the tool. This subsystem is 1.2" in diameter and 2" in length. A force sensor by Omega Engr. (LC 8100-200-5) is used to measure up to 5 lb. At lower frequencies (0.5 up to 2.0 hz.), PID control reduces force errors by 10×. Another tool by MICRON uses 3 DOF piezoelectric manipulator with a 0.016" range and a force capability of 0.22 lb. It can remove slow drift, 10 hz. tremors and sudden jumps. A control loop damper and motion scaling do provide useful error cancellation.

A preferred embodiment of a 2 DOF tool of the type disclosed herein uses an advanced Simplified Parallel Eccentric (SPE) and a Linear Planetary Screw (LPS). The LPS provides linear oscillation, while the SPE provides rotary oscillation whose speed, range, force levels, and other parameters are controlled by the surgeon's voice commands. The LPS uses an extremely small but sophisticated planetary screw transmission. The outer shell of the transmission is driven directly by the rotor of a miniaturized BLDC motor. It provides linear oscillation to the tool. The linear oscillation shaft goes through a SPE by means of a spline. This spline is rotated by a specialized parallel eccentric gear train driven by an external BLDC motor. Both BLDC motors may be piezoelectric, and the materials are preferably MRI compatible.

The oscillating translation/rotation drive shaft passes through an LED optics ring and drives a rotary joint to which is attached a linear slide with bellows. This linear slide then holds a 6 DOF F/T sensor which attaches to the surgical tool with a quick-change interface. This whole system may be about 8" long and 1" in diameter. The sensors generate data which may be transferred wirelessly to a computer with embedded performance maps to rapidly develop commands to the two prime movers. This arrangement may automatically cancel tremors and errors up to 10 hz. Using predictive analytics, these archived commands/responses may be interpreted for better operating criteria (performance objectives), lessons learned for improved training and ultimately guidance for follow-on design. The MICRON tool has already shown an error reduction of 20 to 50%. Hence, with the exceptional actuators and sensors disclosed herein, and with real-time computation based on embedded performance maps and guidance to the surgeon based on visualization of his command/response effectiveness, this handheld tool may offer much better performance than the Micron tool, and may also offer a pathway for continuous improvement.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims. It will also be appreciated that the various features set forth in the claims may be presented in various combinations and sub-combinations in future claims without departing from the scope of the invention. In particular, the present disclosure expressly contemplates any such combination or sub-combination that is not known to the prior art, as if such combinations or sub-combinations were expressly written out.

What is claimed is:

1. An actuator, comprising:
   a parallel eccentric gear train;
   a prime mover having an assembly of piezoelectric elements, wherein the assembly of piezoelectric elements drives said gear train, and wherein the assembly of piezoelectric elements forms a mechanical amplifier; and
   a crankshaft which is driven by said parallel eccentric gear train.

2. The actuator of claim 1, wherein said crankshaft is equipped with first and second eccentrics.

3. The actuator of claim 2, further comprising:
   first and second parallel eccentric gears which are oscillated 180° out-of-phase by said first and second eccentrics.

4. The actuator of claim 1, further comprising:
   an internal gear which is driven by said first and second parallel eccentric gears.

5. The actuator of claim 4, further comprising at least one rotation prevention element which prevents the rotation of said first and second parallel eccentric gears.

6. The actuator of claim 5, wherein said at least one rotation prevention element comprises first and second crosslinks.

7. The actuator of claim 6, wherein said first and second crosslinks mesh with said first and second parallel eccentric gears, respectively.

8. The actuator of claim 7, wherein said first and second crosslinks mesh with said first and second parallel eccentric gears by way of a plurality of tongue and groove surface features collectively defined on the surfaces of said first and second crosslinks and said first and second parallel eccentric gears.

9. The actuator of claim 7, wherein said first and second crosslinks are Oldham couplings.

10. The actuator of claim 1, wherein said actuator is devoid of rolling element bearings.

11. The actuator of claim 1, wherein each of said plurality of piezoelectric elements has a major dimension of at least 0.375 inches.

12. The actuator of claim 1, wherein said crankshaft includes a rotor, wherein said rotor has first and second eccentrics disposed on a surface thereof.

13. The actuator of claim 1, further comprising an output gear and first and second opposing endplates, wherein said output gear is disposed about the periphery of said first and second opposing endplates.

14. The actuator of claim 1, further comprising first and second eccentric gears, wherein each of said first and second eccentric gears has a peripheral surface with a plurality of gear teeth defined therein.

15. The actuator of claim 1, further comprising first and second parallel eccentric gears, first and second eccentrics and an output gear, wherein said first parallel eccentric gear is disposed between said first eccentric and said output gear and meshes with said output gear, and wherein said second parallel eccentric gear is disposed between said second eccentric and said output gear and meshes with said output gear.

16. The actuator of claim 1, further comprising first and second endplates, first and second crosslinks and first and second eccentric gears, wherein said first crosslink engages said first endplate and said first eccentric gear by way of a first set of surface features, and wherein said second crosslink engages said second endplate and said second eccentric gear by way of a second set of surface features.

17. The actuator of claim 1, wherein each of said plurality of piezoelectric elements is contained in a piezoelectric disk.

18. The actuator of claim 1, further comprising first and second parallel, spaced apart endplates, wherein each of said plurality of piezoelectric elements is disposed between said first and second endplates.

19. The actuator of claim 1, wherein said mechanical amplifier amplifies a displacement of the second set of piezoelectric elements contained therein.

20. The actuator of claim 1, wherein said prime mover includes a first set of piezoelectric elements and a second set of piezoelectric elements, wherein the first set of piezoelectric elements drives said gear train, and wherein the second set of piezoelectric elements forms a mechanical amplifier that drives the first set of piezoelectric elements.

\* \* \* \* \*